US011511066B2

(12) United States Patent
Heatherington

(10) Patent No.: US 11,511,066 B2
(45) Date of Patent: *Nov. 29, 2022

(54) RESPIRATORY ASSEMBLY

(71) Applicant: SNAP CPAP, LLC, Chapel Hill, NC (US)

(72) Inventor: Stuart Heatherington, Chapel Hill, NC (US)

(73) Assignee: SNAP CPAP, LLC, Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/011,875

(22) Filed: Jun. 19, 2018

(65) Prior Publication Data

US 2018/0296785 A1     Oct. 18, 2018

Related U.S. Application Data

(63) Continuation-in-part of application No. 15/694,774, filed on Sep. 2, 2017, now Pat. No. 10,905,842, which
(Continued)

(51) Int. Cl.
*A61M 16/06*   (2006.01)
*A61M 16/08*   (2006.01)
(Continued)

(52) U.S. Cl.
CPC .... *A61M 16/0666* (2013.01); *A61M 16/0493* (2014.02); *A61M 16/0605* (2014.02);
(Continued)

(58) Field of Classification Search
CPC .......... A61M 16/0666; A61M 16/0493; A61M 16/0825; A61M 16/0605;
(Continued)

(56) References Cited

U.S. PATENT DOCUMENTS 2,677,371 A    5/1954   Serra
4,782,832 A    11/1988  Trimble et al.
(Continued)

FOREIGN PATENT DOCUMENTS

CN       101653632 A       2/2010
DE    102006016125 A1      10/2007
(Continued)

OTHER PUBLICATIONS

USPTO, Non-Final Office Action for U.S. Appl. No. 14/876,099, dated Dec. 20, 2018.
(Continued)

*Primary Examiner* — Kendra D Carter
*Assistant Examiner* — Arielle Wolff
(74) *Attorney, Agent, or Firm* — NK Patent Law

(57) ABSTRACT

A respiratory assembly is provided. The assembly includes a base engaged with at least one connector and in fluid communication with a hose or fluid source for allowing the gaseous flowthrough between the at least one connector, the base and the hose or fluid source. The assembly further includes a pair of sockets engaged with the at least one connector, and a pair of posts, each post selectively engageable with at least one of the pair of sockets. Each post includes a flange that defines an opening therethrough, the openings in fluid communication with each corresponding socket of the pair of sockets. Each post further includes an adhesive adhered to each flange and configured for sealably engaging a patient's nare.

20 Claims, 23 Drawing Sheets

Related U.S. Application Data is a continuation-in-part of application No. PCT/US2016/055834, filed on Oct. 6, 2016, which is a continuation-in-part of application No. 14/876,099, filed on Oct. 6, 2015, now Pat. No. 10,265,493.

(51) Int. Cl.
*A61M 16/04* (2006.01)
*A61B 5/097* (2006.01)

(52) U.S. Cl.
CPC ......... *A61M 16/0825* (2014.02); *A61B 5/097* (2013.01); *A61M 16/0683* (2013.01); *A61M 16/0816* (2013.01); *A61M 16/0875* (2013.01); *A61M 2016/0661* (2013.01); *A61M 2210/0618* (2013.01); *A61M 2210/0625* (2013.01)

(58) Field of Classification Search
CPC ...... A61M 2016/0661; A61M 16/0875; A61M 16/0816; A61M 2210/0625; A61M 2210/0618; A61M 16/0683; A61B 5/097
See application file for complete search history.

(56) References Cited

U.S. PATENT DOCUMENTS

| | | | |
|---|---|---|---|
| 4,915,105 A | 4/1990 | Lee | |
| 5,116,088 A * | 5/1992 | Bird | A61M 16/08 128/202.27 |
| 5,676,133 A | 10/1997 | Hickle et al. | |
| 5,806,898 A | 9/1998 | Hollnagle | |
| 6,408,850 B1 | 6/2002 | Sudge | |
| 6,571,798 B1 | 6/2003 | Thornton | |
| 7,506,649 B2 | 3/2009 | Doshi et al. | |
| 8,061,357 B2 | 11/2011 | Pierce et al. | |
| 8,215,308 B2 | 7/2012 | Doshi et al. | |
| 8,291,906 B2 | 10/2012 | Kooij et al. | |
| 10,265,493 B2 * | 4/2019 | Heatherington | A61M 16/0825 |
| 2003/0094178 A1 | 5/2003 | McAuley et al. | |
| 2004/0139973 A1 | 7/2004 | Wright | |
| 2004/0216747 A1 | 11/2004 | Jones, Jr. et al. | |
| 2005/0199242 A1 | 9/2005 | Matula, Jr. et al. | |
| 2005/0205096 A1 | 9/2005 | Matula, Jr. et al. | |
| 2006/0042631 A1 | 3/2006 | Martin et al. | |
| 2006/0124131 A1 * | 6/2006 | Chandran | A61M 16/06 128/206.28 |
| 2006/0237017 A1 | 10/2006 | Davidson et al. | |
| 2006/0283461 A1 | 12/2006 | Lubke et al. | |
| 2007/0272249 A1 * | 11/2007 | Chandran | A61M 16/0666 128/206.28 |
| 2007/0283962 A1 | 12/2007 | Doshi et al. | |
| 2008/0041373 A1 | 2/2008 | Doshi et al. | |
| 2008/0223375 A1 | 9/2008 | Cortez et al. | |
| 2009/0032026 A1 | 2/2009 | Price et al. | |
| 2009/0095303 A1 | 4/2009 | Sher et al. | |
| 2009/0101147 A1 | 4/2009 | Landis et al. | |
| 2009/0194109 A1 | 8/2009 | Doshi et al. | |
| 2009/0241961 A1 | 10/2009 | McAuley et al. | |
| 2010/0000534 A1 * | 1/2010 | Kooij | A61M 16/0666 128/204.18 |
| 2010/0229872 A1 | 9/2010 | Ho | |
| 2010/0282263 A1 | 11/2010 | Asada et al. | |
| 2011/0056497 A1 | 3/2011 | Scheiner et al. | |
| 2011/0067704 A1 * | 3/2011 | Kooij | A61M 16/0666 128/207.18 |
| 2011/0253147 A1 * | 10/2011 | Gusky | A61M 16/206 128/207.18 |
| 2013/0098360 A1 * | 4/2013 | Hurmez | A61M 16/142 128/203.12 |
| 2013/0131534 A1 | 5/2013 | Heatherington et al. | |
| 2013/0199537 A1 * | 8/2013 | Formica | A61M 16/0611 128/205.25 |
| 2014/0000614 A1 | 1/2014 | Chang | |
| 2014/0150798 A1 | 6/2014 | Fong et al. | |
| 2016/0317773 A1 | 11/2016 | Buddharaju | |

FOREIGN PATENT DOCUMENTS

| | | |
|---|---|---|
| EP | 0821978 A2 | 4/1998 |
| EP | 3246064 A1 | 11/2017 |
| JP | 57137793 A | 8/1982 |
| JP | 03030777 A | 2/1991 |
| JP | 2013538632 A | 10/2013 |
| WO | 2005076874 A2 | 8/2005 |
| WO | 2007130067 A1 | 11/2007 |
| WO | 2008100860 A2 | 8/2008 |
| WO | 2009117163 A1 | 9/2009 |
| WO | 2014092703 A1 | 6/2014 |
| WO | 2014120271 A1 | 8/2014 |
| WO | 2017062677 A1 | 4/2017 |

OTHER PUBLICATIONS

ISA/KR, PCT International Search Report for PCT/US2018/049109, dated Dec. 28, 2018.
ISA/KR, PCT Written Opinion for PCT/US2018/049109, dated Dec. 28, 2018.
USPTO, Luarca, Margaret M, Non Final Office Action dated Sep. 11, 2018 for U.S. Appl. No. 14/876,099.
EPO, Extended European Search Report for Application No. EP 16854360.1, dated May 10, 2019.
WIPO, International Preliminary Report on Patentability for PCT Patent Application No. PCT/US2016/055834, dated Apr. 10, 2018, 10 pages.
PCT, International Search Report for International Application No. PCT/US2016/055834 dated Jan. 25, 2017.
PCT, Written Opinion for International Application No. PCT/US2016/055834 dated Jan. 25, 2017.
USPTO, Non-Final Office Action in U.S. Appl. No. 15/695,774 dated Sep. 9, 2019.
USPTO, non-Final Office Action in U.S. Appl. No. 15/695,774 dated Dec. 31, 2019.
CNIPA, Office Action in Chinese Patent Application No. 20168055181.5 dated Jan. 6, 2020.
PCT, International Preliminary Report on Patentability in International Application No. PCT/US2018/049109 dated Mar. 3, 2020.
USPTO, Final Rejection in U.S. Appl. No. 15/694,774 dated Mar. 19, 2020.
IP Australia, Examination Report in Australian Application No. 2016334080 dated Jun. 12, 2020, pp. 1-5.
INPI—Brazilian Patent Office, Office Action in Brazilian Application No. BR112018007048-3 dated Jun. 15, 2020.
CNIPA, 2nd Office Action for corresponding Chinese Patent Application No. 201680055181.5, dated May 11, 2020, 19 pages.
JPO, Office Action in Japanese Application No. 2018-518427 dated Sep. 17, 2020.
USPTO, non-Final Office Action in U.S. Appl. No. 15/694,774 dated Aug. 21, 2020.
EPO, Extended European Search Report for European Patent Application No. 19750901.1, dated Jan. 13, 2022, 10 pages.
IP India, Examination Report for corresponding Indian Patent Application No. 201827011815, dated Jun. 1, 2021, 7 pages.
EPO, Partial Supplementary European Search Report for European Patent Application No. 19750901.1, dated Oct. 4, 2021, 12 pages.

* cited by examiner

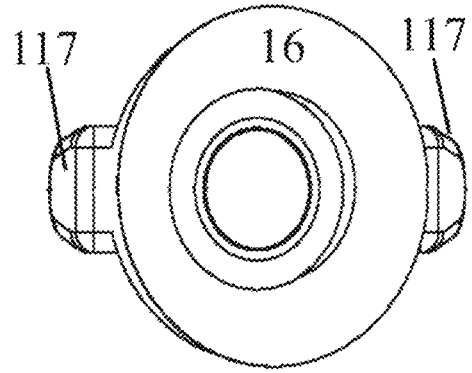
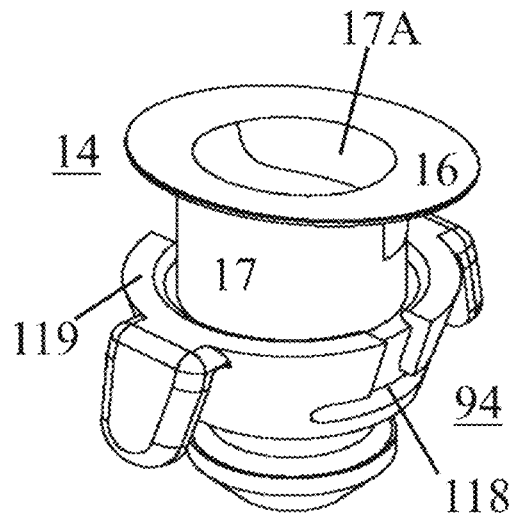
Figure 13A　　　　　Figure 13B
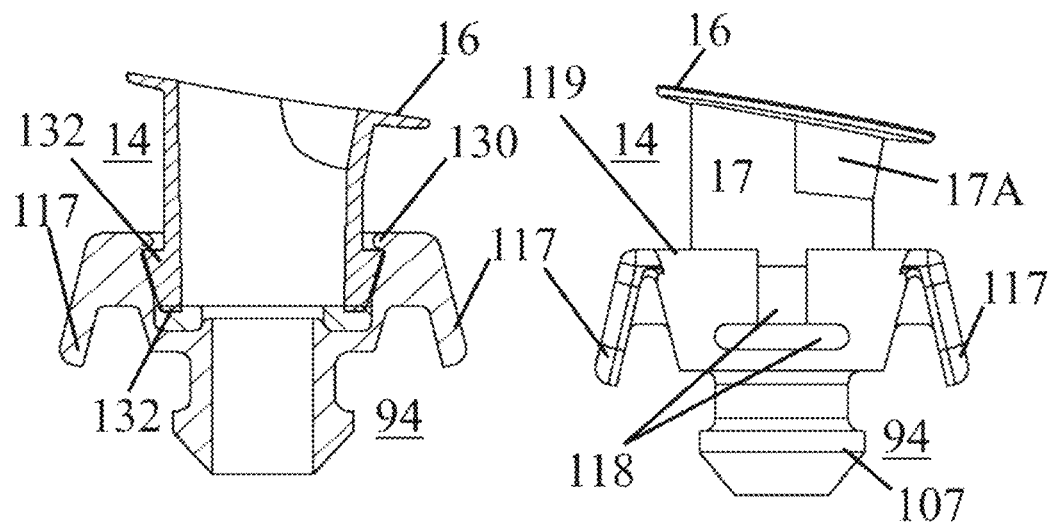
Figure 13C　　　　　Figure 13D

RESPIRATORY ASSEMBLY

CROSS-REFERENCE TO RELATED APPLICATIONS

This application is a continuation-in-part of U.S. patent application Ser. No. 15/694,774, filed Sep. 2, 2017, which is a continuation-in-part of International Application No. PCT/US2016/055834 filed Oct. 6, 2016, which is a continuation-in-part of U.S. patent application Ser. No. 14/876,099 filed Oct. 6, 2015, the entire contents each of which are hereby incorporated by reference.

TECHNICAL FIELD

This disclosure is related to a respiratory assembly, and more particularly a respiratory assembly having a nostril engaging portion for providing sealable engagement with a treatment fluid.

BACKGROUND

Continuous positive air pressure (CPAP) masks are used for treating patients having any number of sleeping or breathing disorders during sleeping. CPAP masks can deliver a treatment fluid, such as ambient air or oxygen enriched air to a patient under a predetermined or desired pressure setting.

CPAP masks suffer from many disadvantages. For example, CPAP masks are bulky, making them less aesthetically and ergonomically pleasing. CPAP masks must provide sealable engagement with the patient's skin in order to maintain a sealed environment for achieving the desired pressure for treatment fluid delivery. This sealable engagement leaves wear marks on the patient's skin and may require undesirable amounts of time for the wear marks to disappear. Accordingly, many patients feel uncomfortable in public until the wear marks have disappeared, and male patients may not be able to shave their faces and female patients not be able to apply makeup until the wear marks have disappeared. These depressions or marks may be the result of the masks enveloping the mouth and/or the nostril, as well as the straps or connections that may be positioned about the patient's head.

Due to the bulky nature of conventional CPAP masks, the masks occupy a large portion of a person's face. This restricts the person's ability to move their head during sleep because laying on the side of one's face may contact the CPAP mask and dislodge the mask from sealable engagement with the patient, thereby evacuating the pressure in the mask assembly. This is undesirable as either the patient is not receiving treatment gases under the ideal pressures or the patient is awakened.

Accordingly, there is a need for an improved CPAP respiratory assembly that addresses the disadvantages associated with conventional CPAP machines and masks. Further, there is a need for a CPAP respiratory assembly that is strapless and maskless, thereby addressing the bulky and mark-forming nature of conventional CPAP machines and masks.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

According to at least one embodiment, a respiratory assembly is provided. The respiratory assembly includes a pair of sockets in fluid communication with a fluid source; a pair of posts, each post selectively engageable with at least one of the pair of sockets, wherein each post includes: a flange that defines an opening therethrough, the openings in fluid communication with each corresponding socket of the pair of sockets; an adhesive adhered to each flange and configured for sealably contacting a patient's nare without penetrating a nostril of the patient.

According to another embodiment, the assembly further comprises hook and loop fasteners for selectively engaging the sockets and the posts to each other.

According to another embodiment, the assembly further comprises a base engaged with at least one connector and in fluid communication with a hose or fluid source for allowing the gaseous flowthrough between the at least one connector, the base and the hose or fluid source; the pair of sockets engaged with the at least one connector.

According to another embodiment, wherein each of the pair of sockets includes pinchers for permitting selective engagement between the sockets and the posts.

According to another embodiment, wherein each pincher includes at least one collar pivotable by relative to the corresponding socket for selectively accepting one of the pair of posts within the corresponding socket and engaging the corresponding post.

According to another embodiment, wherein each pincher further defines a recess between two collars for accepting and aligning the post relative to the socket.

According to another embodiment, wherein each of the pair of sockets further includes a handle for manipulating each socket when accepting and engaging the corresponding post.

According to another embodiment, wherein the adhesive includes a breathable foam for venting of carbon dioxide.

According to another embodiment, wherein the respiratory assembly is maskless and strapless.

According to another embodiment, wherein the system includes two connectors, each engaged with one of the pair of sockets.

According to another embodiment, wherein the base defines four openings for engaging two connectors and two caps.

According to another embodiment, wherein the flange of the posts are angled relative to a post body defined by the posts, each post body selectively engaging the at least one of the pair of sockets.

According to another embodiment, the assembly further comprises vents for titrating fluids.

In some embodiments, the presently disclosed subject matter is directed to a respiratory assembly comprising a base engaged with: at least one connector, wherein the base is in fluid communication with a hose or fluid source for allowing the gaseous flowthrough between the at least one connector, the base, and the hose or fluid source and a pair of sockets engaged with the at least one connector. Each socket defines a collar comprising a socket tip for receiving a respective eyelet that connects to a user's nare and a cavity extending through the collar, wherein the collar has a first mode of operation in which the socket tip is engaged with an eyelet and a second mode of operation in which the socket tip is not engaged with the eyelet through retraction of the socket tip in response to manipulation by a user.

In some embodiments, the socket tip includes a lip configured to releasably engage with a proximal projection, a distal projection, and a depression that extend about a circumference of the eyelet.

In some embodiments, the lip has an inner diameter that is less than the outer diameter of the distal and proximal projections.

In some embodiments, the proximal projection comprises a barb.

In some embodiments, the socket is constructed from an elastomeric material. In some embodiments, the elastomeric material is selected from natural rubber, synthetic rubber, polyurethane, acrylic, vinyl, nitrile rubber, butadiene rubber, styrene-butadiene rubber, acetate, and combinations thereof.

In some embodiments, the eyelet comprises a flange that is connected to a nasal strip configured to releasably attach to a user's nare.

In some embodiments, the eyelet comprises a body defined by a proximal projection and a distal projection that extend about the circumference of the body, and a depression positioned between the proximal and distal projections.

In some embodiments, the base defines four openings for engaging two connectors and two caps.

In some embodiments, the respiratory assembly includes vents for titrating fluids.

In some embodiments, the presently disclosed subject matter is directed to a method of providing fluid to a patient's nasal passages. The method comprises releasably attaching the socket tip of a respiratory assembly to an eyelet that connects to a patient's nare. The respiratory assembly comprises: a base engaged with at least one connector, wherein the base is in fluid communication with a hose or fluid source for allowing the gaseous flowthrough between the at least one connector, the base, and the hose or fluid source. The base further comprises a pair of sockets engaged with the at least one connector, wherein each socket defines a collar comprising a socket tip for receiving a respective eyelet that connects to the patient's nare. The base further comprises a cavity extending through the collar; wherein the collar has a first mode of operation in which the socket tip is engaged with an eyelet and a second mode of operation in which the socket tip is not engaged with the eyelet through retraction of the socket tip in response to manipulation by a user. The method includes releasably attaching the eyelet to the patient's nare, and initiating the flow of fluid from the fluid source, whereby fluid is provided to the patient's nasal passages.

In some embodiments, the fluid is ambient air or oxygen enriched air.

In some embodiments, the socket tip includes a lip configured to releasably engage with a proximal projection, a distal projection, and a depression that extend about a circumference of the eyelet.

BRIEF DESCRIPTION OF THE DRAWINGS

The foregoing summary, as well as the following detailed description of preferred embodiments, is better understood when read in conjunction with the appended drawings. For the purposes of illustration, there is shown in the drawings exemplary embodiments; however, the presently disclosed invention is not limited to the specific methods and instrumentalities disclosed. In the drawings:

FIGS. 13A-13D illustrate a socket assembly and a post according to one or more embodiments disclosed herein;

FIG. 20b is a side plan view of the eyelet of FIG. 20a.

DETAILED DESCRIPTION

The presently disclosed invention is described with specificity to meet statutory requirements. However, the description itself is not intended to limit the scope of this patent. Rather, the inventors have contemplated that the claimed invention might also be embodied in other ways, to include different steps or elements similar to the ones described in this document, in conjunction with other present or future technologies.

Figure 1:
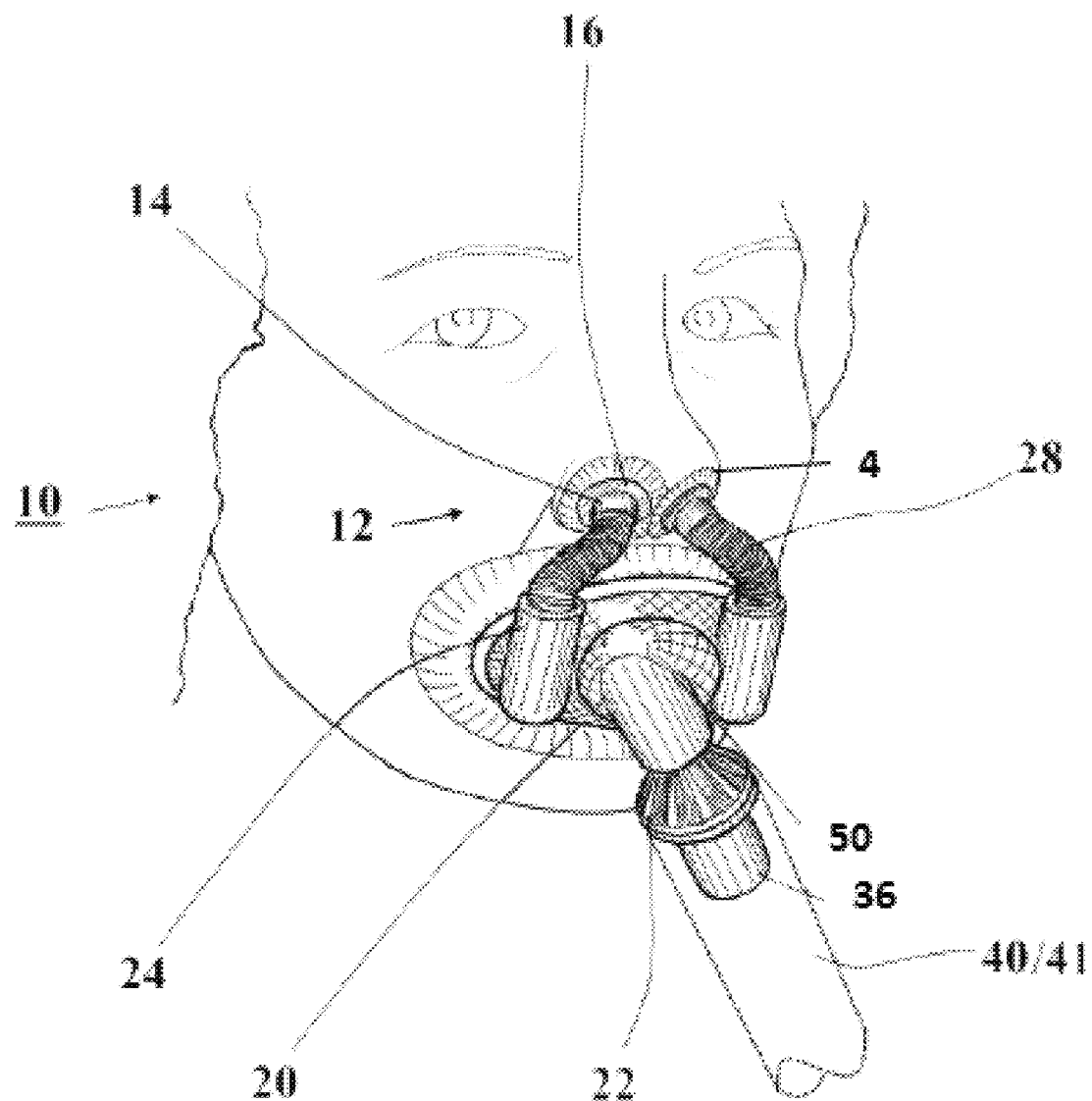
FIG. 1 illustrates a perspective view of a respiratory mask and a patient for being treated according to one or more embodiments disclosed herein.

FIG. 1 illustrates a respiratory assembly installed upon a patient 1 according to at least one embodiment. Such an embodiment is described in detail in U.S. patent application Ser. No. 13/672,946 filed Nov. 9, 2012 and issued as U.S. Pat. No. 9,149,595. The respiratory assembly is generally designated as 10 throughout the drawings. The assembly 10 includes a nasal assembly 12. The nasal assembly 12 may include at least one post 14 with a nasal engaging portion 16 on or about a first end thereof for delivering treatment gases to the nasal cavity of the patient 1. The post 14 may be configured for providing a flush, sealable engagement with the patient's nares.

The respiratory assembly 10 may include a mask assembly 20 having an inlet 22 for receiving treatment gases from a fluid source 41 and at least one receptacle 24 for being sealably engaged with the post 14. The fluid source 41 may be a continuous positive airway pressure (CPAP) machine, a fluid tank, a humidifier, or some other fluid source. The post 14 may be selectively engageable with the receptacle 24, such that the engagement is permanent or only when desired by the patient. Alternatively, the post 14 may be selectively engageable directly with a tube 28 carrying treatment gases therethrough.

Figure 2:
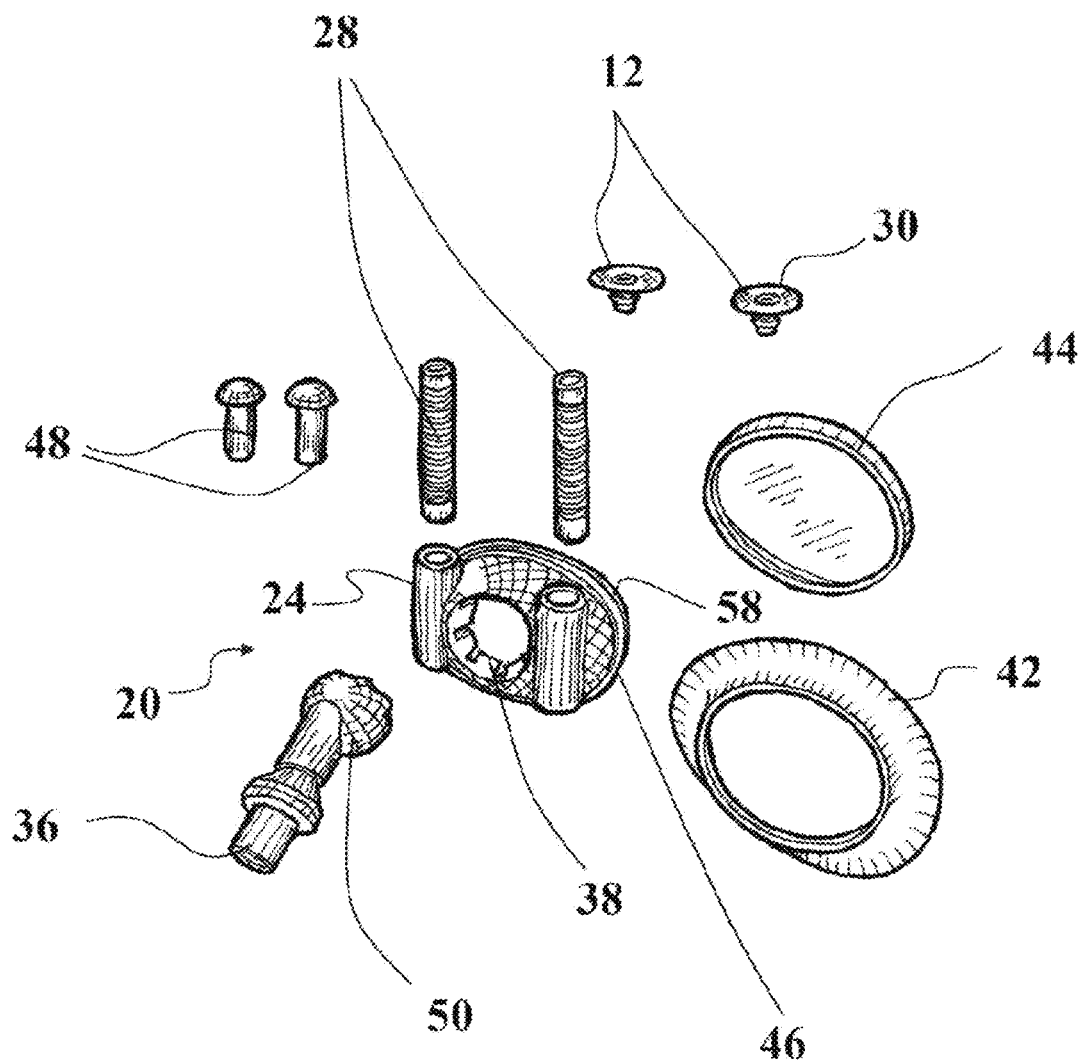
FIG. 2 illustrates a perspective view of a mask according to one or more embodiments disclosed herein.

As illustrated in FIG. 2, the inlet 22 may include a swivel joint 36 for allowing swiveling movement of the inlet 22 about the mask assembly 20. The inlet 22 may be a hose 40 for providing flowthrough of treatment gases from the fluid source 41 to the inlet 22.

The receptacle 24 may include a tube 28 configured for flexible movement to position the nasal assembly 12 to various sizes of respective patients' noses. The mask assembly 20 may be configured for sealable engagement with the patient's mouth by an adhesive pad 42 selectively engageable therewith and carried by the mask body 46. Within the mask body 46 may be defined a chamber 58 through which treatment gases flow from the inlet 22. In this manner, in one operative condition, the mask assembly 20 may be sealably engaged with both the patient's mouth area while the nasal assembly 12 may be also engaged with the patient's nares or nasal area. In this operative condition, treatment gases may be being supplied to both the patient's mouth and their nasal area simultaneously. The mask body 46 may further define a socket recess 38 for cooperating with a joint described further herein.

Alternatively, panel 44 may be provided for sealable engagement with the mask assembly 20 in order to seal off the chamber 58 so that treatment gases do not pass into the area surrounding the patient's mouth and instead pass only through to the nasal assembly 12. In this manner, the one or more devices 10 disclosed herein may be appropriately configured for both CPAP applications in which the patient receives treatment gases to both their mouth and nose and in CPAP applications where the patient receives treatment gases to only their nose. Additionally, one or more plugs 48 may be provided for use with the mask assembly 20 to seal receptacles 24 if the patient does not desire use of the nasal engaging configuration provided herein. Accordingly, the respiratory assembly 10 described herein may have three distinct modes of operation: one in which treatment gases are being supplied to the patient's mouth only, one in which treatment gases are being supplied to the patient's nose only, and one in which treatment gases are being supplied to the patient's nose and mouth.

Figure 3:
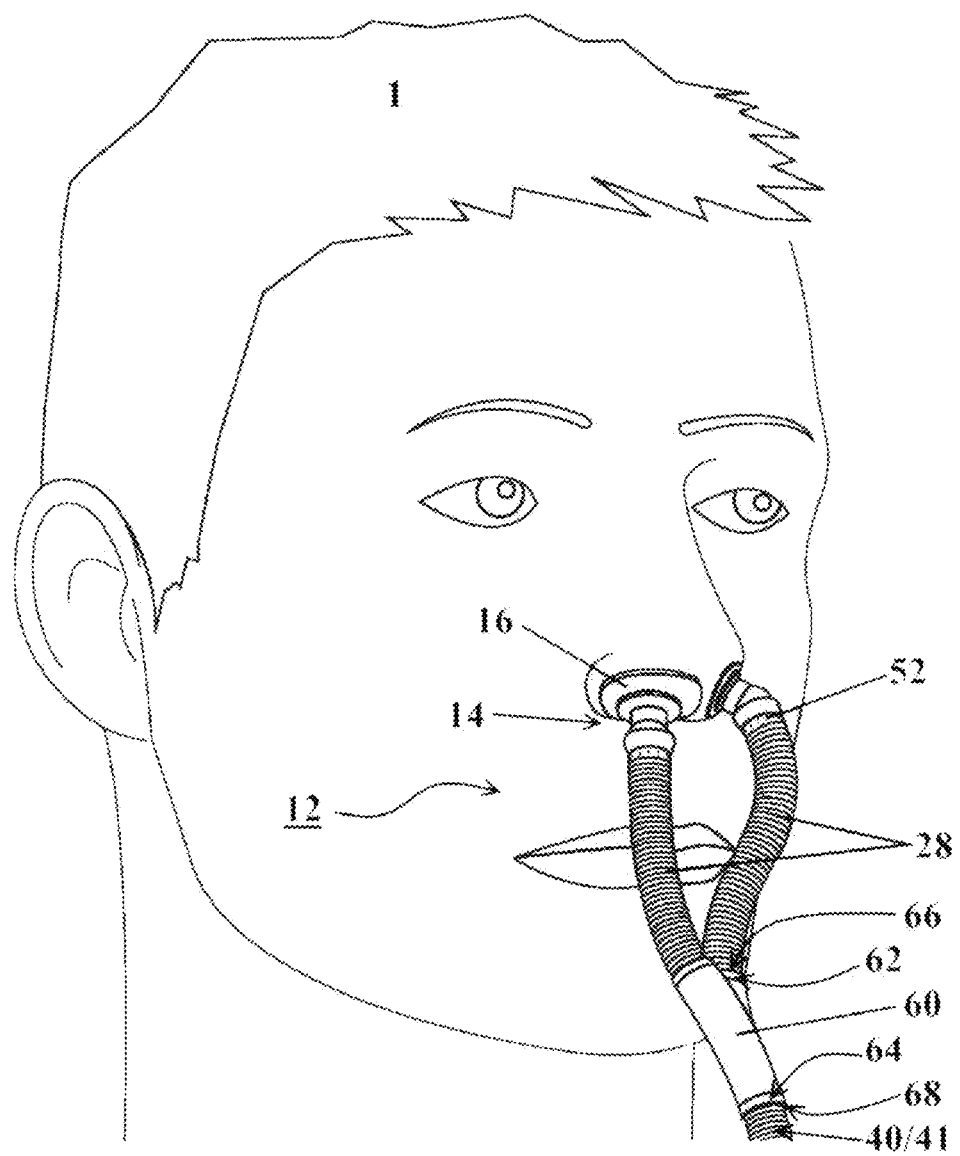
FIG. 3 illustrates a perspective view of a nasal assembly and a patient for being treated according to one or more embodiments disclosed herein.
Figure 4:
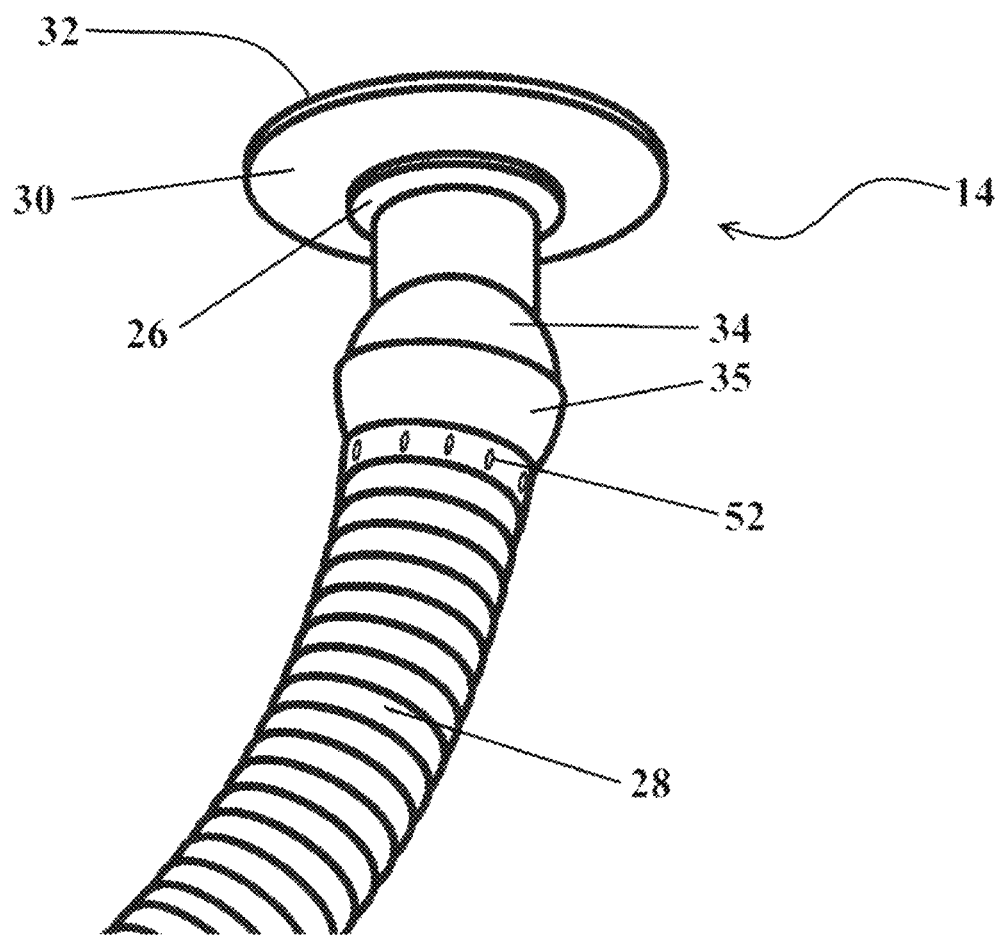
FIG. 4 illustrates a perspective view of a portion of a nasal assembly according to one or more embodiments disclosed herein.

In one or more embodiments, the inlet 22 may further include a ball and socket joint 50 as illustrated in FIG. 2, with ball being represented as 50 and socket recess being represented by 38. The ball and socket joint allows for rotational movement of the inlet 22. The ball 50 may define a plurality of vents 52 for allowing flow of treatment gases therethrough. The vents 52 may be adjustable in size and location such that manipulation of all exhaled fluids such as carbon dioxide from the patient is controlled and titratable such that the flow rate of fluids can be altered to a desired setting. In alternative embodiments, as depicted in FIGS. 3 and 4, each tube 28 of the pair of tubes 28, each post 14 of the pair of posts 14, or both may include vents or vent opening 52 for allowing gaseous flowthrough. Further, the vent openings 52 may be adjustable for titration of gases therethrough. In some embodiments, vents 52 may be comprised of polymeric fibers, membranes or webs with extremely small thickness from nanoscale to microscale. Polymeric fibers may be produced by electro spinning PTFE (polytetrafluoroethylene).

In one or more embodiments, the mask body 46 may include an adjustable mechanism that allows the tubing from the post 14 to be altered, moved or elevated to accommodate a patient's facial structure, primarily the distance between the nose and the oral housing port on or inside body 46, thereby allowing for ideal facial angles and facial length that might add to a patient's comfort. To further increase comfort, usability and effectiveness of the respiratory assembly 10, nasal assembly 12 and/or mask assembly 20, software and printing capabilities can be employed to customize the shape and contour of the various components respiratory assembly 10 and/or nasal assembly 12. For example, but not limited to, the nasal engaging portion 16 of the nasal assembly 12 may be specifically contoured to fit each nasal passage of the patient 1. Such customization can be achieved by digitally scanning the features of a patient's face to create a CAD model or for 3D printing. Further, various portions, or the whole of, the mask body 46 and/or adhesive pad 42 may be customized to more effectively fit the facial contours of the patient 1. Such customization may be applied to any component of the respiratory assembly 10, including, but not limited to, the nasal assembly 12, the base 90, the connector 91, the socket 94, the cleat assembly 80, the sheet 30, and/or the splitter 60.

FIG. 3 illustrates a nasal assembly 12 installed upon a patient 1 according to at least one embodiment. The nasal assembly 12 may include a pair of tubes 28, each in gaseous communication with a hose 40 or a fluid source 41. The pair of tubes 28 and the hose 40 may be unitarily formed. Alternatively a splitter 60 may be positioned between each of the pair of tubes 28 and the hose 40 or the fluid source 41. The splitter 60 may be engaged with each of the pair of tubes 28 and the hose 40 or fluid source 41 for allowing the gaseous flowthrough between each of the pair of tubes 28 and the hose 40 or the fluid source 41. The splitter 60, pair of tubes 28 and hose 40 may be unitarily formed.

The engagement of the splitter 60 with the tubes 28 and/or hose 40 or fluid source 41 may be achieved using a number of different structural configurations. Some structural configurations may permit greater pivotal movement between the elements 28, 40, 60, while at the same time maintaining a sealable engagement for preventing leakage of gas therefrom. The splitter 60 may have two tube-engaging ends 62 for engaging the tubes 28 and one source-engaging end 64 for engaging the hose 40 or fluid source 41. The tubes 28 may include a tube splitter receiver 66. The hose 40 or fluid source 41 may include a source splitter receiver 68. In some embodiments, the receivers 66, 68 or engaging ends 62, 64 may be circumferentially extending structures engaged with corresponding recess structures. Alternatively, the receivers 66, 68 or engaging ends 62, 64 may be splitter or tube sockets engaged with corresponding tube or splitter ball joints for allowing pivotal movement of the tubes 28 about the splitter 60.

In at least one embodiment, such as the embodiment depicted in FIG. 4, each post 14 of the nasal assembly 12 may include an extending portion 34 for selectively engaging a respective receiving portion 35 of the pair of tubes 28. The engagement of the post 14 with the receptacle 24 or tube 28 may be achieved using a number of different structural configurations. The extending portion 34 may be a circumferentially extending portion for selectively engaging a respective recess receiving portion 35. Alternatively, the extending portion 34 may be a post ball joint and the receiving portion 35 being a tube socket, and wherein the post ball joint 34 and the tube socket 35 are configured for selective engagement for allowing pivotal movement of the pair of tubes 28 about each of the pair of posts 14, as depicted in FIG. 4. Another alternative embodiment may include the extending portion 34 being a post socket and the receiving portion 35 being a tube ball joint, wherein the post socket 34 and the tube ball joint 35 are configured for selective engagement for allowing pivotal movement of the pair of tubes 28 about each of the pair of posts 14.

According to some embodiments, the nasal assembly 12 includes a pair of posts 14. FIGS. 5A and 5B illustrate the nasal assembly 12 in greater detail according to at least one embodiment. The post 14 may include a flange 26 configured for engaging with a sheet 30 having an adhesive 32 applied thereon, or alternatively, a layer of adhesive 32, or a layer of adhesive inclusive of a sheet 30, for being adhered and providing sealable engagement with the nostrils of the patient 1. The sheet 30 may have any desired shape, and may preferably include an opening therein for allowing flowthrough in an opening 29 defined in the post 14. The adhesive 32 may be a pressure sensitive adhesive such that the sheet 30 may be adhered and removed from the patient's nostrils as desired. The post 16 may include an extending portion 34 on a second end thereof that is configured for selective engagement with the at least one receptacle 24 or corresponding tube 28 of the pair of tubes 28.

The adhesive 32 (and/or sheet 30) may have varying thicknesses, adhesive strengths and flexibility. The thickness, adhesive strength and flexibility may vary between each adhesive 32 and/or may vary within each individual adhesive 32 itself. For example, the flexibility of the adhesive 32 may be more rigid about the nostril-engaging portions, while more flexible elsewhere. The adhesive 32 may be comprised of a foam medical tape, a surgical tape and/or a hypoallergenic tape. The adhesive 32 may comprise a hydrocolloid tape 18 and/or may include a polyurethane reactive layer that confirms more with the nostril as the patient's body temperature warms up the adhesive 32. The adhesive 32 may include a polyvinyl chloride or polyolefin foam tape and/or an acrylate adhesive layer. In some embodiments, the adhesive 32 may include a cloth layer for adhering to the post 14 using an adhesive substance or tape. The adhesive 32 may include a foam layer between the adhesion to the nare and the post 14. The foam layer may permit $CO_2$ venting. Further, the foam layer may permit flexibility between the post 14 and nare without disengaging from either.

In some embodiments, each post 14 of the pair of posts 14 may include a flange 26 that defines an opening 29 therein, the openings 29 in gaseous communication with each corresponding tube 28 of the pair of tubes 28. Further, an adhesive 32 or layer of adhesive 32 may be applied to each post 14, each post 14 configured for sealably engaging a patient's nare. The adhesive 32 may be applied to a sheet 30 positioned on a nasal facing side of the post 14, or the adhesive may be applied directly to the flange 26 of the post 14. The adhesive 32 may be pressure sensitive. In some embodiments of the invention, the posts 14 described herein may be used in combination with a micro-CPAP device having micro-blowers, where positive and negative charges collapse plates into engagement with each other, forcing air to and through the posts 14 into the nostril of the patient.

Figure 6:
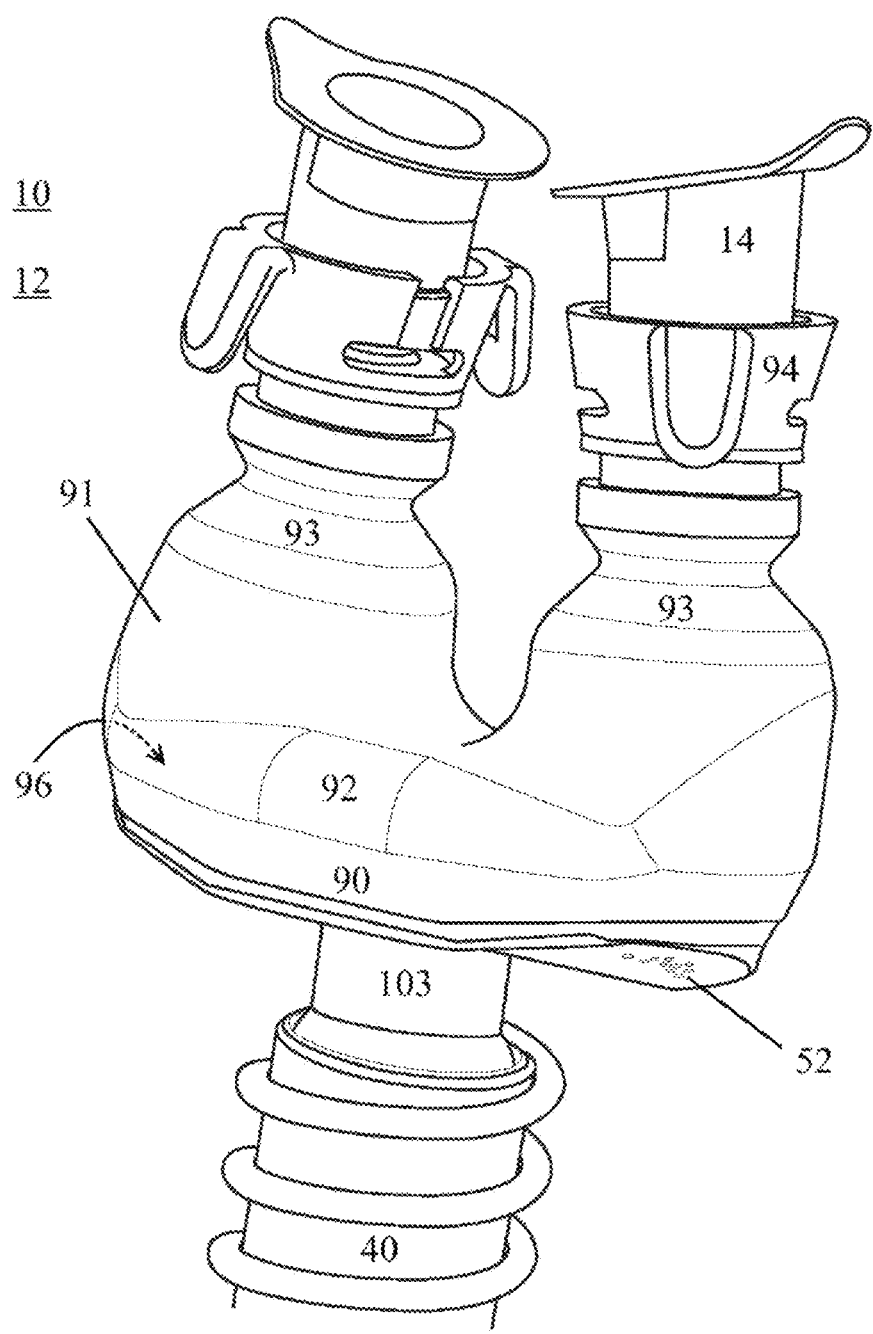
FIG. 6 illustrates a perspective view of respiratory assembly having a base and a single connector according to one or more embodiments disclosed herein.
Figure 8:
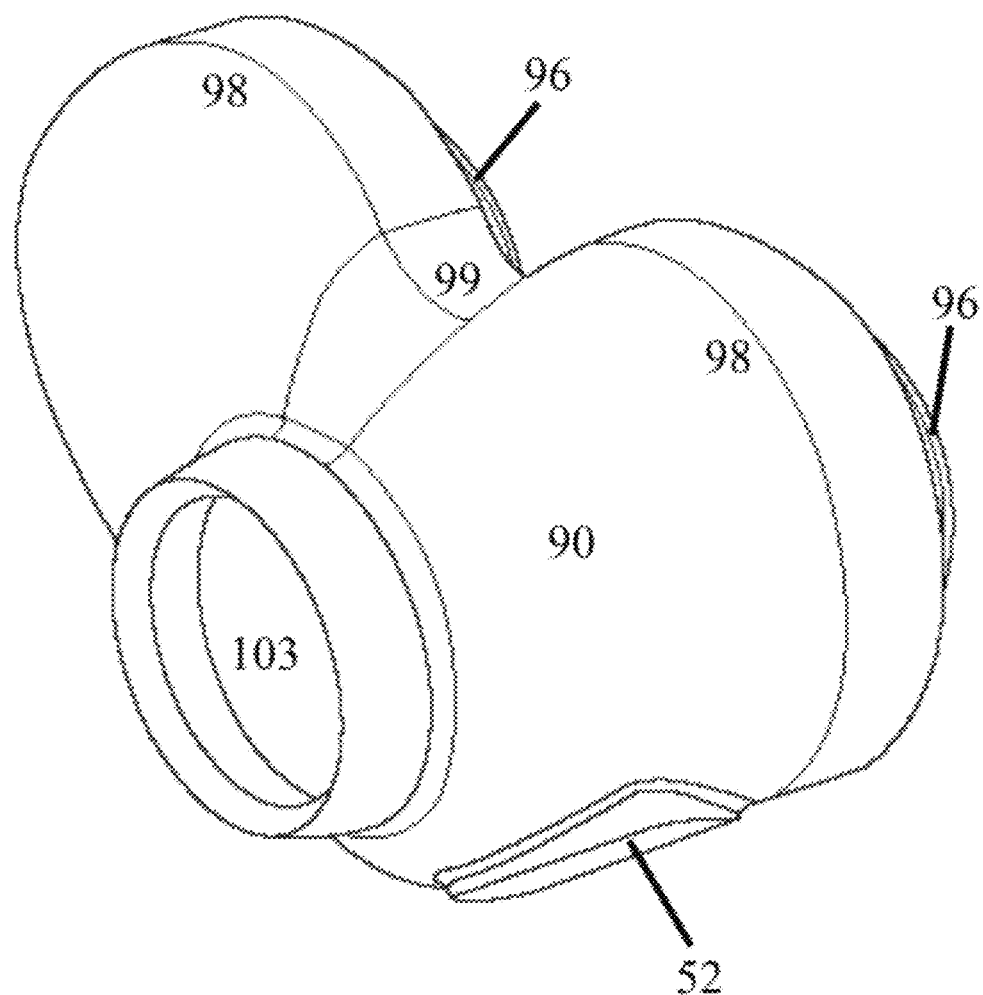
FIG. 8 illustrates a perspective view of a base of a respiratory assembly having two base openings according to one or more embodiments disclosed herein.
Figure 9:
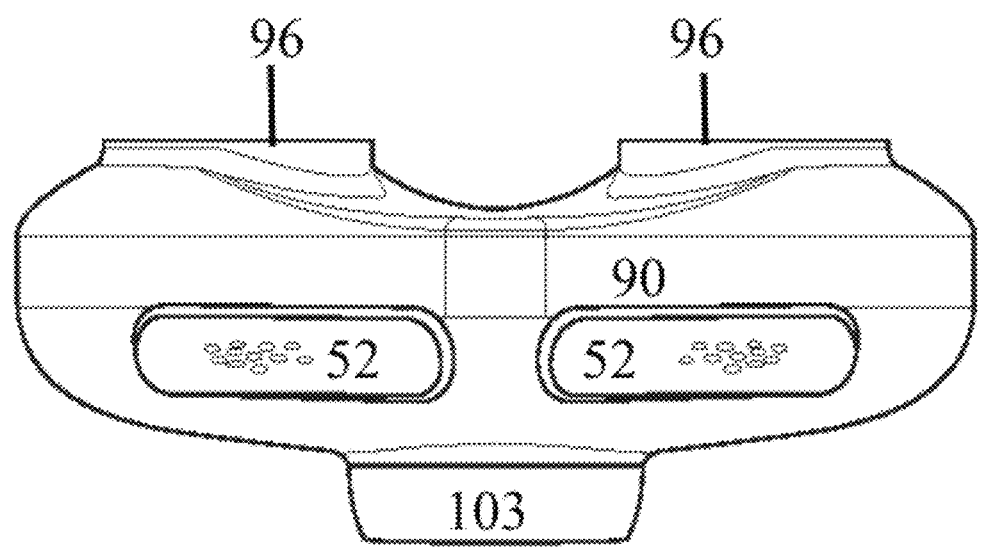
FIG. 9 illustrates a bottom view of a base of a respiratory assembly having two base openings according to one or more embodiments disclosed herein.
Figure 11:
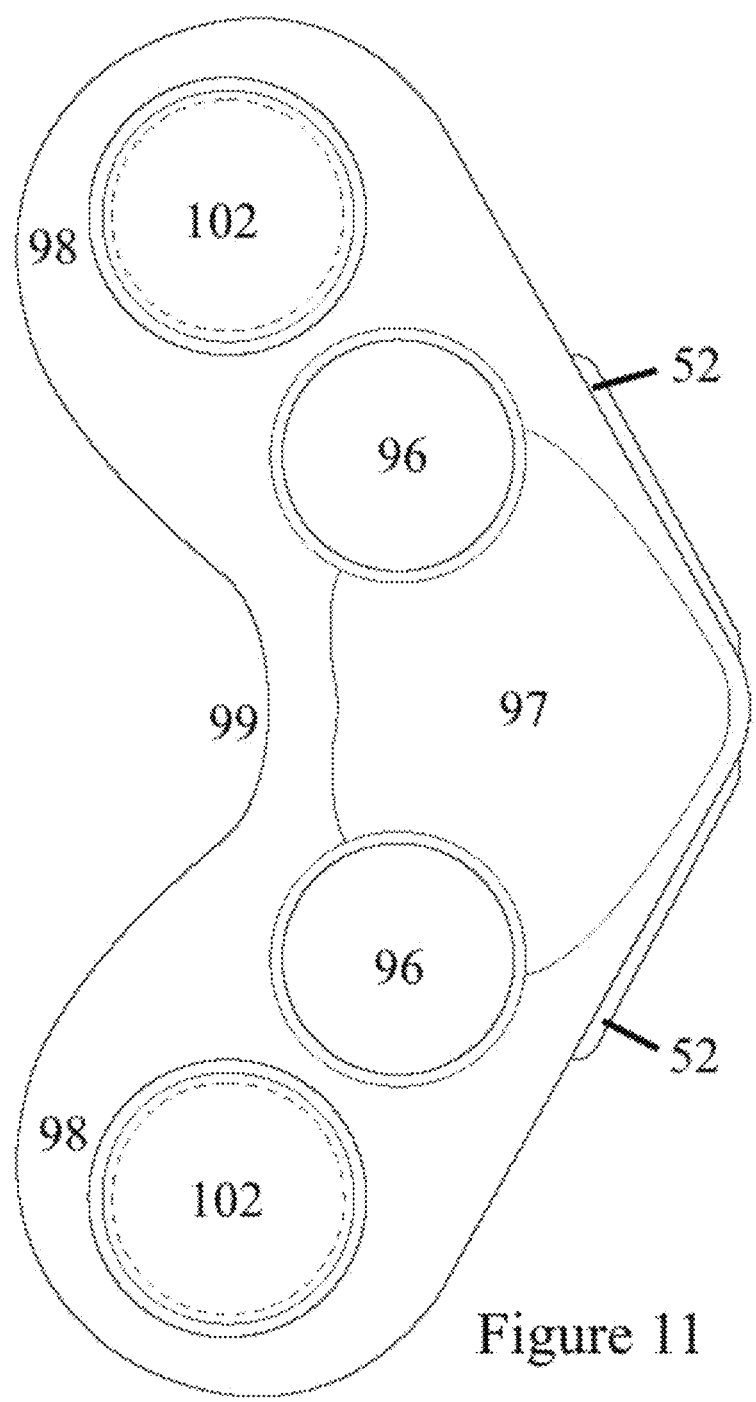
FIG. 11 illustrates a back view of a base of a respiratory assembly having four base openings and two caps according to one or more embodiments disclosed herein.

FIG. 6 illustrates a perspective view of respiratory assembly 10 having a base 90 and a single connector 91 according to one or more embodiments disclosed herein. Notably, the embodiments of FIGS. 6, 8 and 11 are both strapless and maskless—a significant advantage over the prior art, where straps and masks often leave marks on the patient's body. The base 90 may include any number of vents 52. For example, as is illustrated in FIG. 9, the vents 52 may be positioned on the bottom side of the base 90. The base 90 may further include or define a base tube engagement 103 for selectively engaging or coupling to a hose 40 or fluid source 41. The engagement or coupling between the base tube engagement 103 and the hose 40 or fluid source 41 may permit full rotation of the two in relation to each other. The base 90 and base tube engagement 103 may be unitarily formed or formed separately. The base tube engagement 103 may involve any of the engagements described herein, including but not limited to a ball and socket joint, snap engagement, pinch engagement, cleat engagement or other form of engagement. The base tube engagement 103 may include vents 52 or may include a textured or contoured surface for easier maneuverability and operation of the respiratory assembly 10.

The vents 52 of the present invention may be positioned proximal to any of the regions where fluid flow occurs. For example but not limited thereto the vents 52 may be placed on the base 90, connector 91, posts 14, socket 94, base tube engagement 103, etc. The vents 52 may be manufactured using a 3D thermoplastic printing process. The vents 52 may be comprised of microscopic pores. The microscopic pores may be created using a matrix of very thin fibrils. The fibrils may be comprised of polytetrafluoroethylene (PTFE).

Figure 16A:
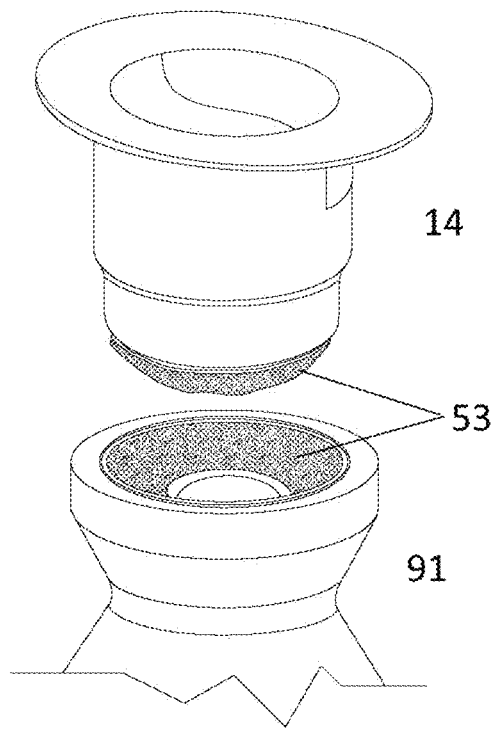
FIG. 16A illustrates a perspective view of a connector and post having a hook and loop engagement according to one or more embodiments disclosed herein.
Figure 16B:
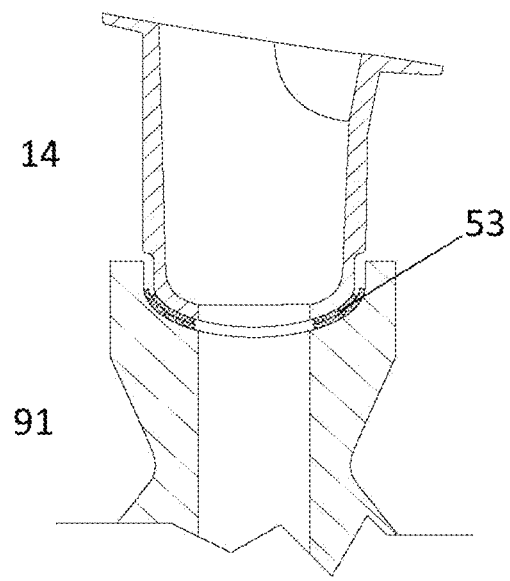
FIG. 16B illustrates a cross-sectional view of a connector and post having a hook and loop engagement according to one or more embodiments disclosed herein.

In other embodiments, the vents 52 may be comprised of hook and loop fasteners 53. For example, but not limited thereto, the hook and loop fasteners 53 may act as connections between various components of the respiratory assembly 10. Turning to FIG. 16, an embodiment of the invention is shown where hook and loop fasteners 53 acting as vents 52 are used to connect the connector 91 to the post 14. By using hook and loop fasteners 53 as the selective engaging connection between various components of the respiratory assembly 10, such as between the connector 91 and post 14, the assembly 10 thereby permits exhaled carbon dioxide to exit the assembly 10. In some embodiments, the use of hook and loop fasteners 53 as vents 52 would permit the assembly 10 to be free of other vents 52, such as the vents depicted in FIGS. 6 and 9.

The base 90 and single connector 91 may be unitarily constructed or constructed separately. For example, the base 90 may be comprised of a hard plastic and the connector 91 may be comprised of silicone. The base 90, socket 94, posts 14 and/or other components of the respiratory assembly 10 may be comprised of a plastic, for example but not limited to polypropylene or polyethylene, which may be of food or medical grade quality. The possibility of unitary or separate construction, and the inclusion of plastics and silicone, may additionally apply to the embodiments depicted in FIGS. 8 and 11, for example, and other embodiments described herein. The connector 91 of FIG. 6 defines a connector body 92 and two connector arms 93. The connector arms 93 may each be selectively engageable or coupled with a socket 94. The socket 94 may engage or couple the interior of the connector arm 93 (see FIG. 6), the exterior of the connector arm 93 or both the interior and the exterior. In one embodiment, the socket 94 may engage the connector arm 93 by sliding into a grooved cavity of the connector arm 93 (and/or socket 94). In one embodiment, the socket 94 may engage the post 14.

A base 90 may be provided for receiving the liquid flow from the hose 40 or fluid source 41. The base 90 may further define at least one base opening 96. For example, FIG. 6 depicts an embodiment wherein the base includes a single base opening 96 for selectively engaging or coupling to the connector 91. In other embodiments, such as FIGS. 8 and 11, for example, the base may include more than one base opening 96—two in FIG. 8 and four in FIG. 11. Any number of base openings 96 may be included for providing various configurations adapted to the contours of various patients 1. Further the engagement or coupling of the one or more base openings 96 and the one or more connectors 91 may be effected using any of the engagements described herein.

Figure 7:
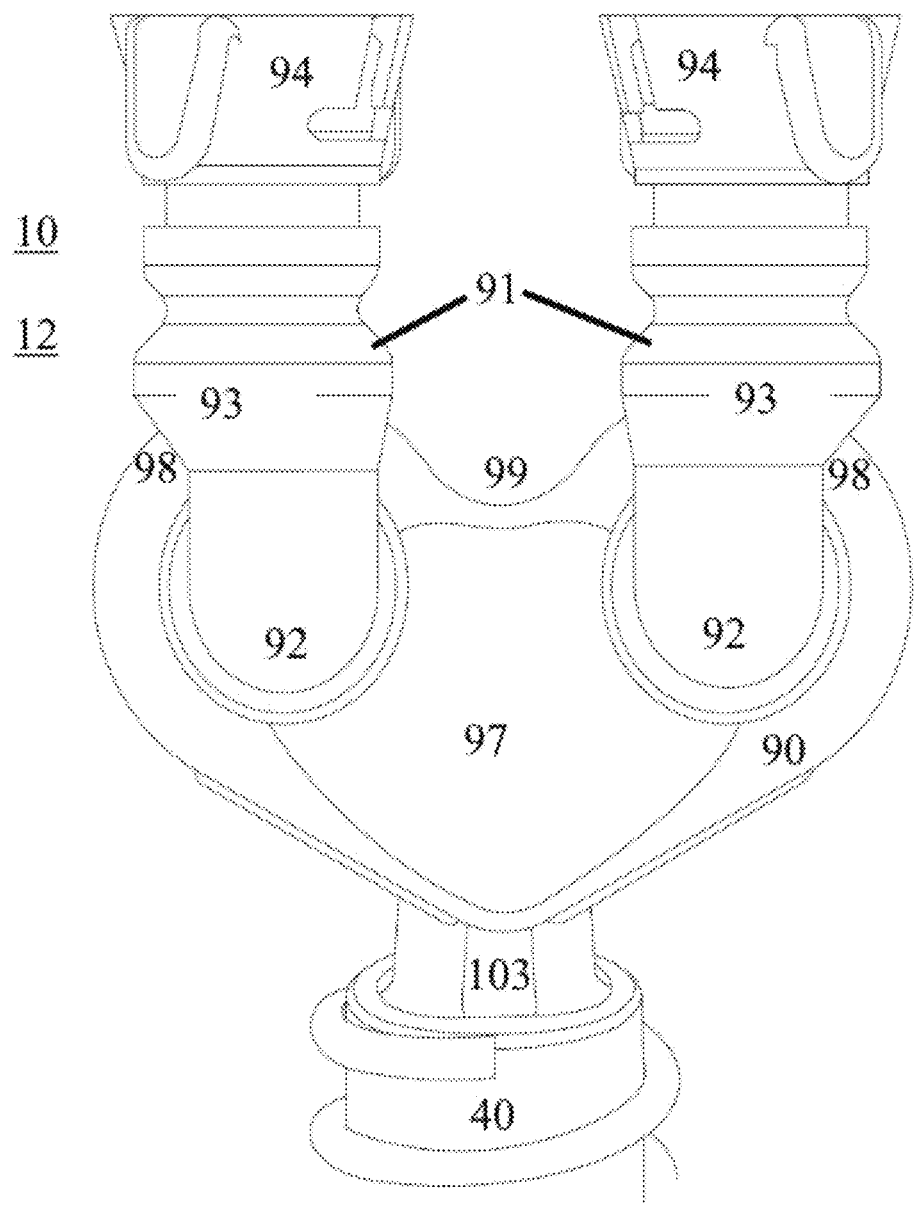
FIG. 7 illustrates a back view of respiratory assembly having a base and two connectors according to one or more embodiments disclosed herein.

FIG. 7 illustrates a back view of respiratory assembly 10 having a base 90 and two connectors 91 according to one or more embodiments disclosed herein. The base 90 may define a base concavity 97 for allowing freer movement of the patient's lips, or access thereto, by being shaped away from the patient's face when the respiratory assembly 10 is engaged with the patient's nares. Further, the base 90 may include one or more base bulges 98 and a base dip 99 for minimizing the volume being used by the respiratory assembly 10, thereby allowing greater access to the patient's face and easier manipulation of various components of the respiratory assembly 10.

The base 90 of FIG. 7 defines two base openings 96 for selectively engaging or coupling to each of at least two connectors 91. More than two connectors 91 may be provided such that the connectors 91 may be interchanged as desired, for varying the shape (and therefore airflow), angle (and therefore position) and/or type, which may include any of the engagements described herein. Each connector 91 may be shaped and comprised of materials for deformability, such that the connector arms 93 may be flexed in relation to the connector body 92. Sockets 94 may be included in the respiratory assembly 10 for selectively engaging or coupling to the connectors 91.

Figure 10:
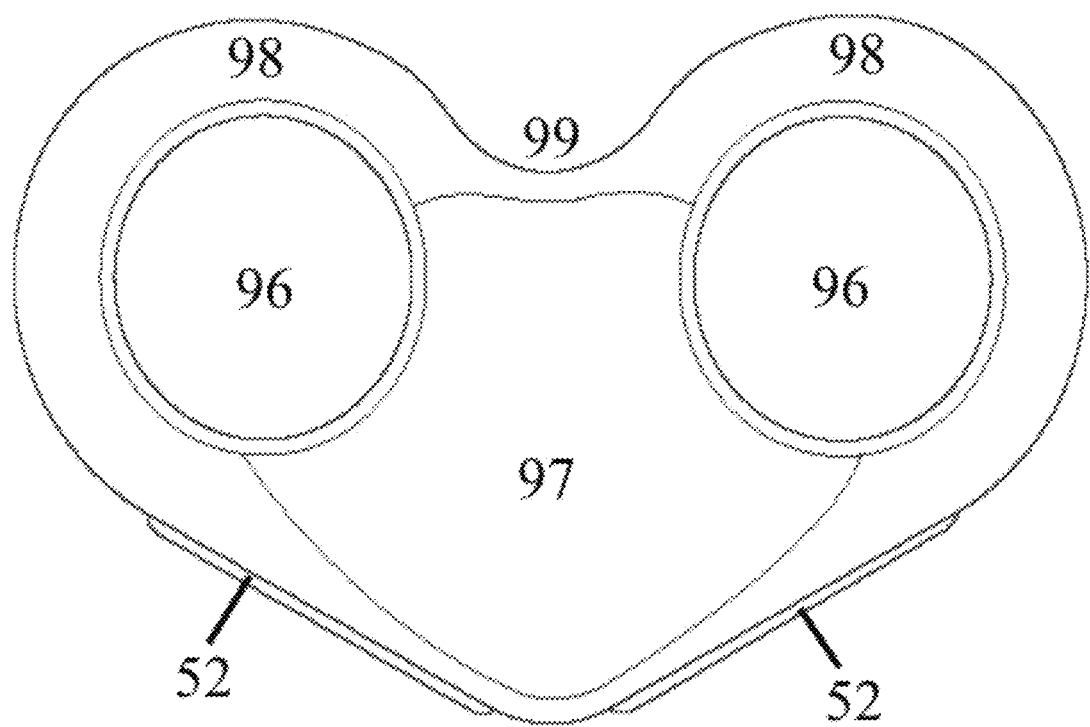
FIG. 10 illustrates a back view of a base of a respiratory assembly having two base openings according to one or more embodiments disclosed herein.

FIG. 8 illustrates a perspective view of a base 90 of a respiratory assembly 10 having two base openings 96 and a base tube engagement 103 according to one or more embodiments disclosed herein. FIG. 9 illustrates a bottom view of a base 90 of a respiratory assembly 10 having two base openings 96 according to one or more embodiments disclosed herein. FIG. 10 illustrates a back view of a base 90 of a respiratory assembly 10 having two base openings 96 according to one or more embodiments disclosed herein.

FIG. 11 illustrates a back view of a base 90 of a respiratory assembly 10 having four base openings 96 and two caps 102 according to one or more embodiments disclosed herein. The two caps 102 may cover the base openings 96 when not in use and/or when the base openings 96 are not engaged or coupled to connectors 91. The base openings 96 may be similarly sized and shaped such that connectors 91 may be interchanged and repositioned freely amongst each of the openings 96. Such customization permits a patient to selectively engage or couple the connectors 91 to any two openings 96 for a best fit to the patient's nare. By permitting cleat engagements or ball and joint engagements or any other engagement permitting multiple positioning, and/or by providing angled posts 14 and/or connectors 91, the connector 91, connector arm 93 and/or posts 14 may be positioned to best fit the patient's nare when the respiratory assembly 10 is engaged.

Figure 5:
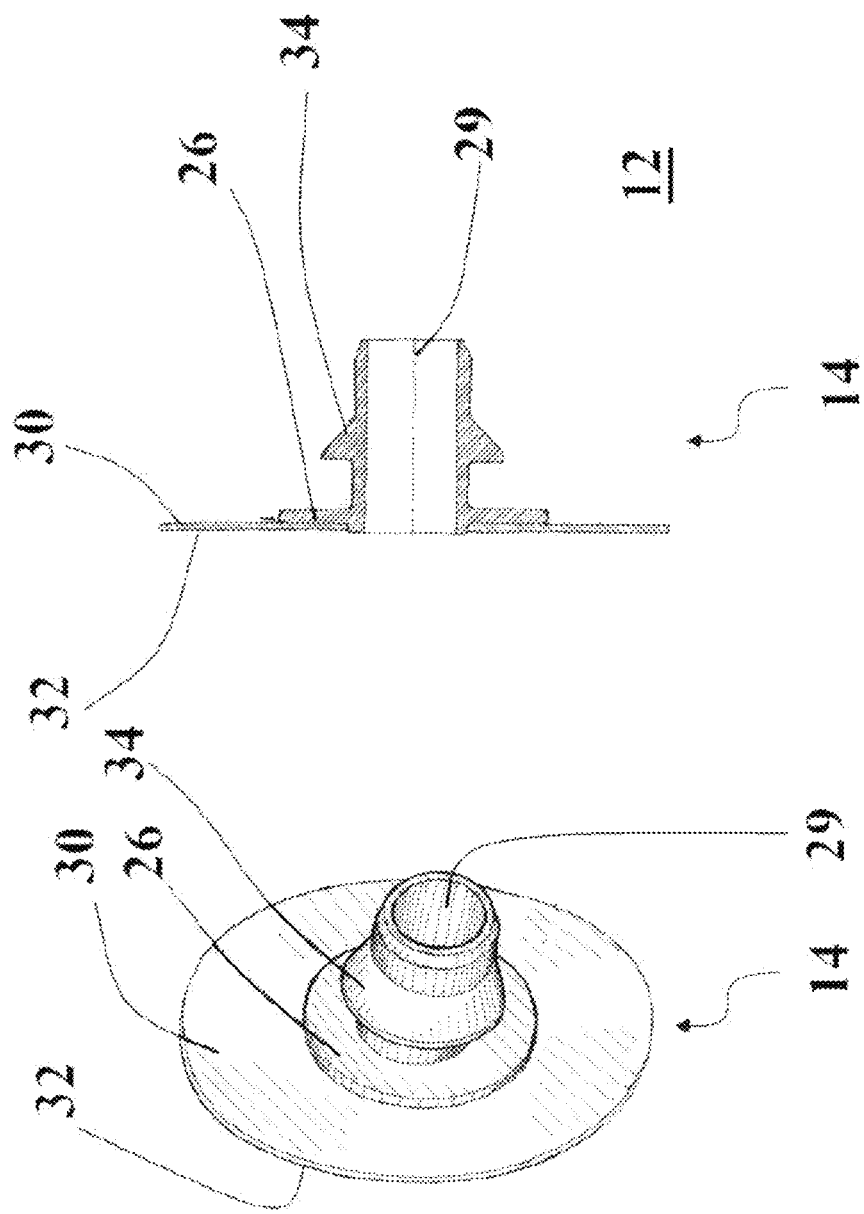
FIGS. 5A and 5B illustrate respective perspective and side views of a nasal assembly for use with a respiratory mask according to one or more embodiments disclosed herein.
Figure 12:
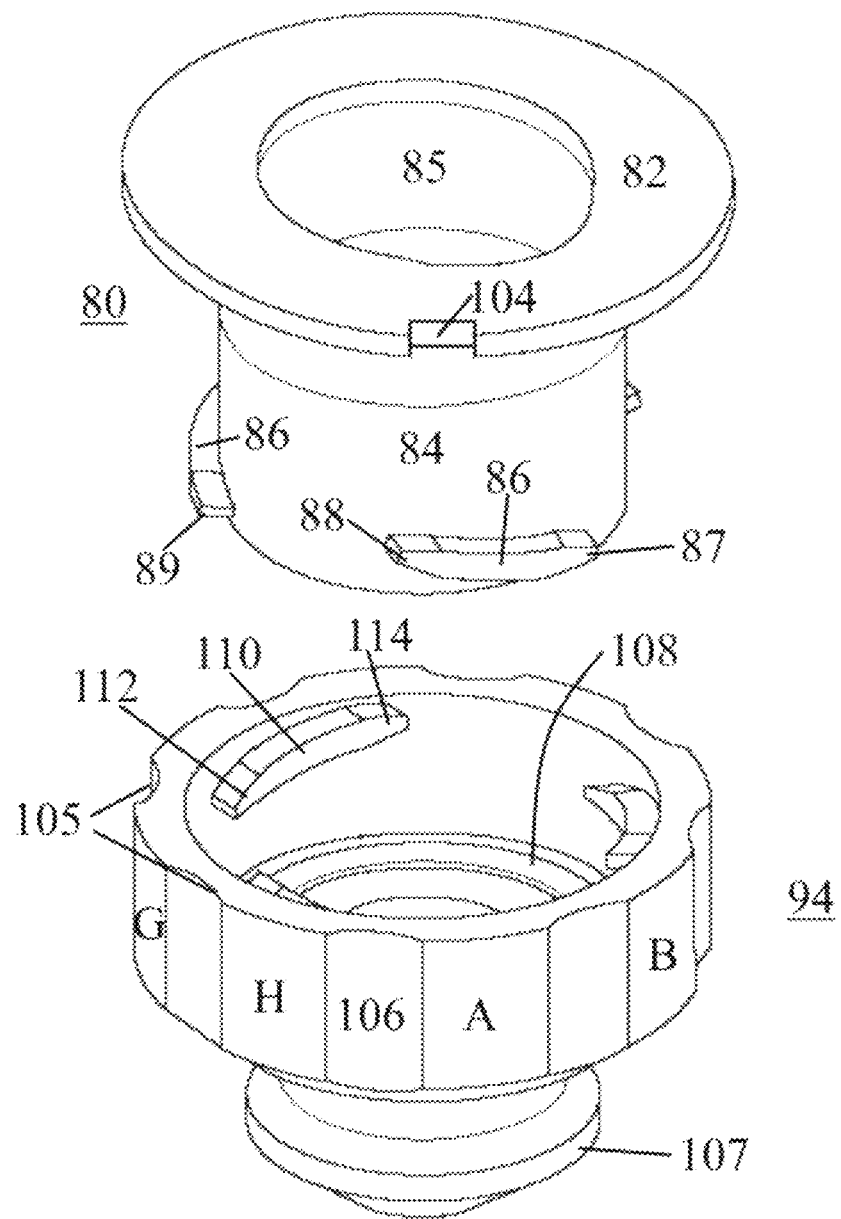
FIG. 12 illustrates a cleat assembly and rotateable socket assembly according to one or more embodiments disclosed herein.
Figure 14A:
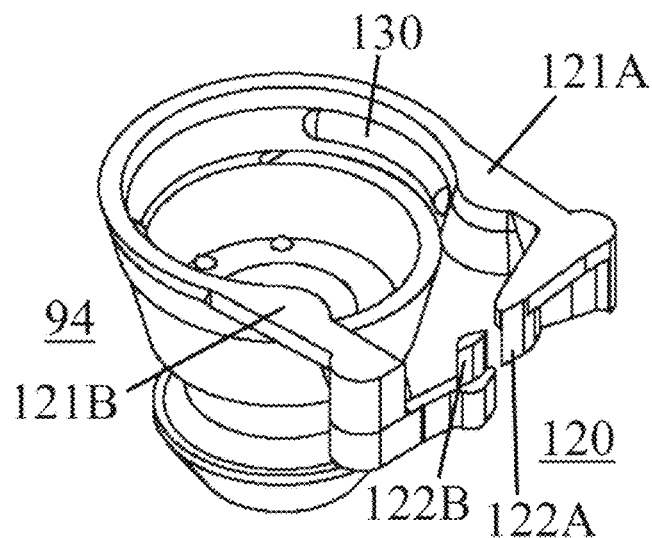
FIG. 14A illustrates a perspective view of a socket assembly having a clamp lock according to one or more embodiments disclosed herein.
Figure 14B:
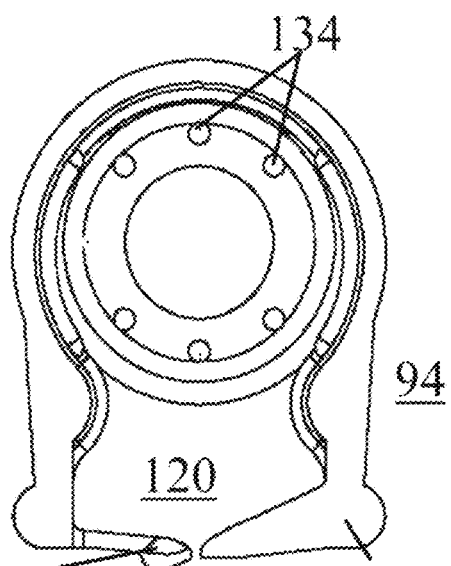
FIG. 14B illustrates a top view of a socket assembly having a clamp lock according to one or more embodiments disclosed herein.
Figure 14C:
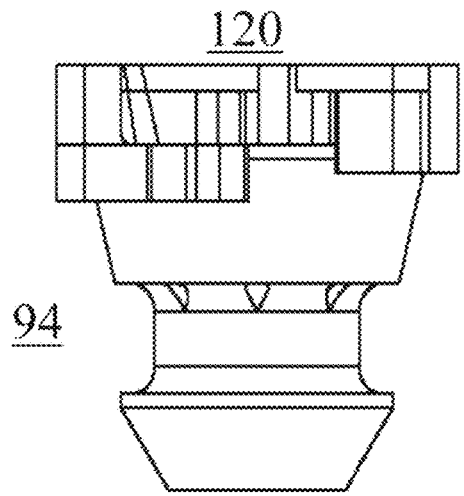
FIG. 14C illustrates a side view of a socket assembly having a clamp lock according to one or more embodiments disclosed herein.
Figure 14D:
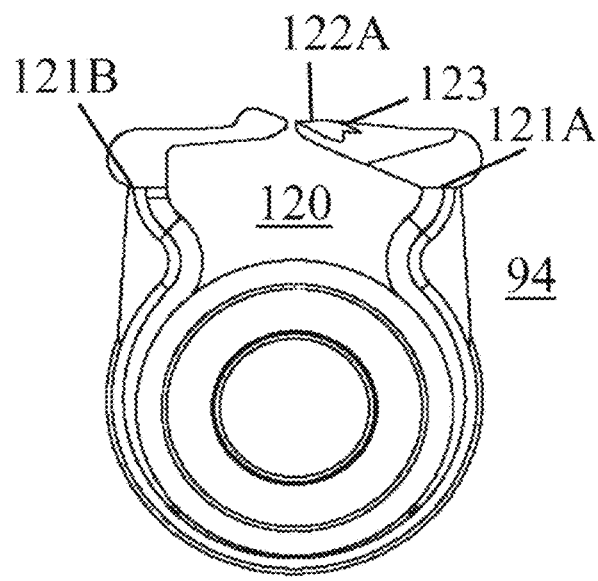
FIG. 14D illustrates a bottom view of a socket assembly having a clamp lock according to one or more embodiments disclosed herein.

FIG. 12 illustrates a cleat assembly 80 and rotateable socket assembly 94 according to one or more embodiments disclosed herein. The sheet 30 of the respiratory assembly 10 may be embedded with a cleat assembly 80, wherein the cleat assembly 80 defines a cleat flange 82 extending between layers of the sheet 30. Alternatively, the sheet 30 and/or adhesive 32 may be applied to a nasal-facing side of the cleat flange 82 of the cleat assembly 80, similar to the nasal engaging portion 16 of the post 14 described herein. The sheet 30, nasal engaging portion 16 and/or cleat flange 82 may be formed to create various shapes in order to fit the numerous types of nares 4 and nostrils 3 of patients. For example, in FIG. 6 the sheet 30 is substantially circular about the nare 4 and extends outward on one side in a triangular manner with a curved apex; such an embodiment provides a greater surface area for adhering to the patient 1. In FIG. 5, the sheet 30 is substantially circular. Throughout the description, cleat flange 82 and nasal engaging portion 16 may be interchangeable used. In other embodiments, the sheet 30, nasal engaging portion 16 and/or cleat flange 82 may be radially undulating, concave or convex so as to conform to the nostril in a conforming manner. Upon application to the patient 1, the sheet 30 and/or cleat flange 82 may overlap between the nares 4 for providing additional support and adhesion. The cleat flange 82 may be similarly shaped and arranged.

The cleat flange 82 of the cleat assembly 80 may be rigid for providing support or flexible for conforming to the shape of the patient's nare 4 and nostril 3. The cleat assembly 80 may further define cleat extension 84 extending from a central or inner portion of the cleat flange 82 and away from the patient 1. The cleat extension 84 may be substantially cylindrical, or may be alternatively shaped, for engaging a post 14 or socket 94 of the nasal assembly 12. The cleat extension 84 may define a plurality of cleat ridges 86 within the interior of the cleat extension 84—the cleat opening 85—and/or the exterior of the cleat extension 84. The cleat ridges 86 may each define a distal end 87 positioned further from the cleat flange 82 than the proximal end 88 defined by the cleat ridge 86. The distal and proximal ends 87, 88 may be arranged for permitting either clockwise or counterclockwise rotation of the post 14 or socket 94 in relation to the cleat assembly 80. Further, the cleat ridges 86 may define a tapered edge 89 on the distal end 87 and/or the proximal end 88 for facilitating smooth rotation and locking of the cleat assembly 80 and the post 14 or socket 94.

In alternative embodiments, the cleat ridges 86 and post or socket ridge 110 may be L-shaped and the cleat assembly may further a spring-based ring (not shown) positioned on the cleat flange 82. During engagement of the post 14 or socket 94 with the cleat assembly 80, the ridges may be pushed past each other and the post 14 or socket 94 may be twisted, then, upon release by the patient, the spring-based ring would 'lock' the cleat assembly 80 and post 14 or socket 94 into place. Socket ridge 110 may define a proximal socket end 112 and a distal socket end 114 similar to the proximal and distal ends 87, 88 of the cleat ridge 86.

Although a socket 94 is depicted in FIG. 12, a post 14 may similarly be selectively engageable with the cleat assembly 80. The socket 94 or post 14 may include position identifiers (A-H) for permitting the patient to selectively engage the socket 94 or post 14 into a particular desired position by lining up the desired position identifier (A-H) with the cleat position identifier 104. The socket 94 or post 14 may further define gripping features 105 for easily rotating the socket head 106. The socket head 106 may be freely rotatable about the socket base 107. In other embodiments (FIGS. 13A-D), the socket base 107 may be shaped for engagement with the connector 91 and/or connector arm 93. Further, the socket 94 or post 14 may include a deformable o-ring 108 for sealing the engagement or coupling of the socket 94 or post 14 to the cleat assembly 80 when engaged. In one embodiment, where the socket 94 engages or couples to the exterior of the connector arm 93, the connector arm 93 may extend within the socket 94 and define an o-ring 108 for sealing the socket-post 94-14 engagement or coupling.

FIGS. 13A-D illustrate a socket assembly 94 and a post 14 according to one or more embodiments disclosed herein. The post 14 may include a nasal engaging portion 16 which is angled in relation to the post body 17 for enhanced positioning of the nasal engaging portion 16 in relation to a nare. The angle may be 15 degrees or any degree between 0 and 45. The angle may be created by having a portion of the post body 17 'bulge' outwards at an angle, as is depicted in FIGS. 13B and 13C. The intersection of the bulge 17A and the post body 17, or the entire bulge 17A itself, may be flexible or deformable and may be comprised of differing material than the other portions of the post body 17. Alternatively, the post body 17 may remain substantially cylindrical, having a top portion 'sliced' at an angle.

The socket assembly 94 may include one or more pinchers 117 for engaging and disengaging the socket 94 from the post 14. The pinchers 117 may extend from a collar end 119 of the socket 94 distal the connector 91 and/or socket base 107. The pinchers 117 may extend from the collar 119 at an angle for providing leverage to the pincher 117 when being 'pinched', therefore enabling the collar 119 of the socket to be deformed away from the post 14 for easy release. A pincher bridge may extend from between the pincher 117 to the collar 119 and below the collar 119 for providing leverage to the collar 119 when the pincher 117 is pinched, instead of merely permitting the pincher 117 to pivot about the connection between the pincher 117 and collar 119.

A socket cavity 118 may be defined by the socket 94 for permitting deformation of the collar 119 when the pinchers 117 are pinched. For example, in FIG. 13D, the socket cavity 118 extends between the collars 119 of the socket 94 and horizontally beneath the collars 119 for permitting deformation of the collar 119 when the pinchers 117 are pinched. Pinching involves placing pressure on the one or more pinchers 117, either individually or simultaneously, so that a distal end of the pinchers 117 are flexed towards the socket 94, thereby lifting a proximal end of the pincher 117, the collar 119, and/or the collar bead 130 and permitting the release of the barb 132 of the post 14, for example.

FIGS. 14A-14D illustrates a socket assembly 94 having a clamp lock 120 according to one or more embodiments disclosed herein. The clamp lock 120 may include two clamp extensions 121. The first clamp extension 121A may defined a first clamp mound 122A and the second clamp extension 121B may define a second clamp mound 122B. One or both of the clamp mounds 122 may include a clamp ridge 123 for permitting the clamp mounds 122 to be lockingly engaged when the extensions 121 are pinched together. Once engaged, the clamp mounds 122 may be disengaged with a subsequent pinch. In one embodiment, pinching the extensions 121 together engages the bead 130 with the post 14 for securing the post 14 in position. The post 14 may define positioners (small protrusions on the underside of the post, distal from the nasal engaging portion 16) for further securing the post 14 position and resisting rotation of the post 14 when the positioners are engaged with the position apertures 134 defined by the socket 94.

Figure 15:
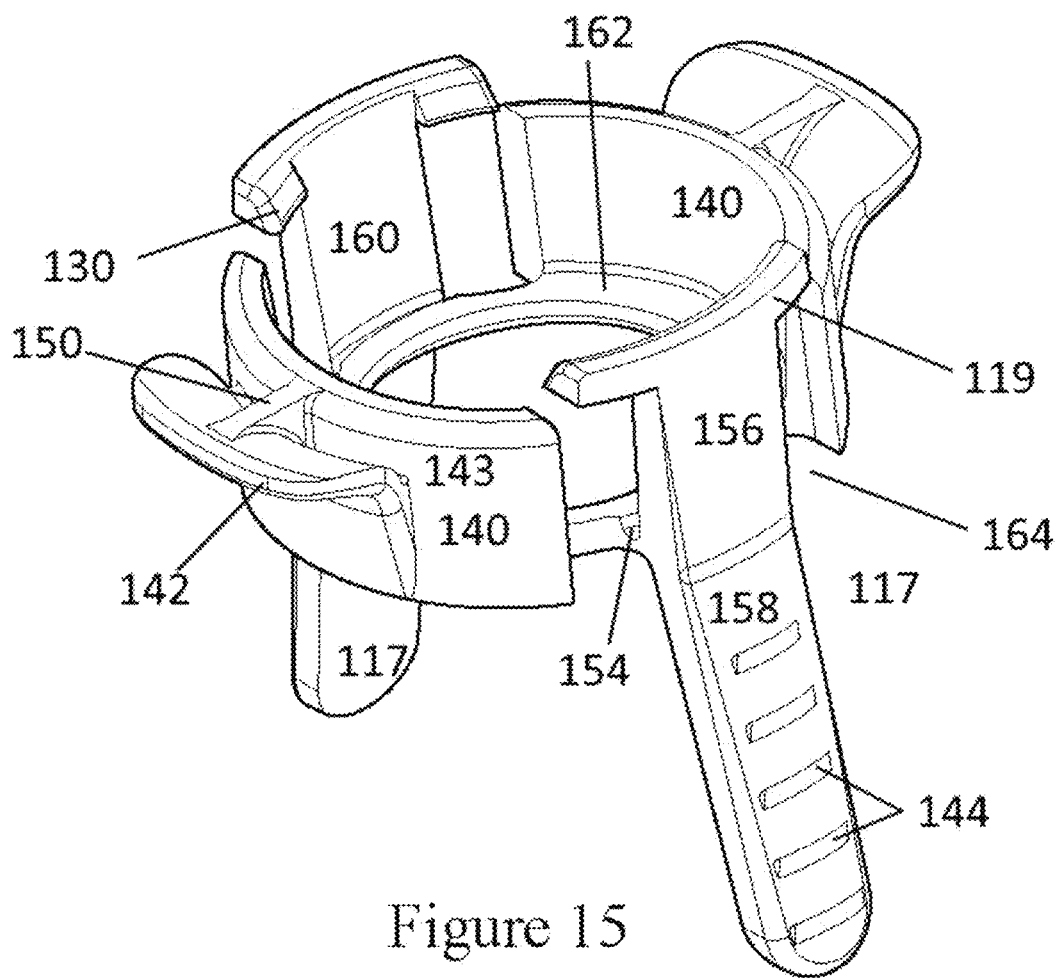
FIG. 15 illustrates a perspective view of a socket having pinchers and tabs according to one or more embodiments disclosed herein.

FIG. 15 illustrates a perspective view of a socket 94 having pinchers 117 and a handle portion 140 according to one or more embodiments disclosed herein. A socket 94 may include any number of pinchers 117. In FIG. 15, two pinchers 117 are positioned opposite each other on the socket 94 and are coupled to the socket 94 along a pincher groove 154 proximal a sealing ring 162 of the socket 94. The pincher groove 154 may be configured for flexing to permit the pinchers 117 to be easily maneuvered. Each pincher 117 may include a pincher body 156 extending from the groove 154 and/or the sealing ring 162 of the socket 94 towards a collar 119. Extending in the opposite direction of the body 156 may be a pincher arm 158 for pivoting the collar 119 and pincher body 156. In some embodiments, the pinchers 117 may define gripping features 144 thereon. The gripping features 144 may include ridges, grooves, or other frictional elements for improving grip.

The pinchers 117 may define a collar 119 configured for accepting and gripping a post 14 when the post 14 is slidingly engaged with the collar of the socket 94. The collar 119 may define one or more collar beads 130 positioned internally of the collar 119 and pincher 117 for selectively engaging the post 14. In some embodiments, the engagement of the collar bead 130 with the post 14, and/or the barb 132 of the post 14, may produce an audible 'snap' sound so as to alert the user that engagement has been effected. The audible sound is particularly advantageous because the user may not be able to visually inspect the engagement of the post 14 and the socket 94 when positioned beneath the user's nose, for example. The pinchers 117 may define a pincher recess 160 extending along an internal portion of the pincher body 156 and the collar 119 for accepting and aligning a portion of the post 14 when the post 14 is slindingly engaged with the socket 94; the pincher recess 160 may extend between two collar beads 130. The interior of the pincher body 156 may define a second pincher recess on either side of the pincher recess 160 for aligning the socket 94 and post 14 engagement and coupling. The second pincher recess may be shaped as an arc of a circle having a diameter greater than the circle defining the arc of the interior of the handle body 143.

The sealing ring 162 of the socket 94 may engage the post 14 when the post 14 is coupled to the socket 94 using the collar 119 of the pinchers 117. The socket 94 may further define a handle portion 140 positioned between the pinchers 117 and extending from the sealing ring 162 of the socket 94, or from a length below the sealing ring 162. The socket 94 may define a void 164 between the pinchers 117 and the handle portion 140 for permitting the pinchers 117 to be manipulated without interference by an engagement with the handle portion 140. The void 164 may extend through a portion of the sealing ring 162 as well.

The handle portion 140 may define a handle tab 142 extending externally therefrom for sliding the socket 94 into engagement with the pinchers 94. By using the handle portion and/or the handle tab 142 instead of the pinchers 117, the audible click of the pinchers 117 is much more likely to occur and be heard, confirming coupling engagement of the socket 94 and post 14. A handle bridge 150 may be defined between the handle tab 142 and the handle body 143 for supporting the handle tab and lessening the flexibility of the handle tab 142 when pressure is applied. There may be more than one handle bridge 150 for each handle tab 142. There may be a single handle bridge 150 positioned centrally along a length of the handle tab 142. The handle tab(s) 142 may be sloped away from the handle body 143, and may include a curved slope for conforming to the shape of a finger—the curve may extend across a length and/or a width of the handle tab 142 of the handle portion 140.

Figure 17A:
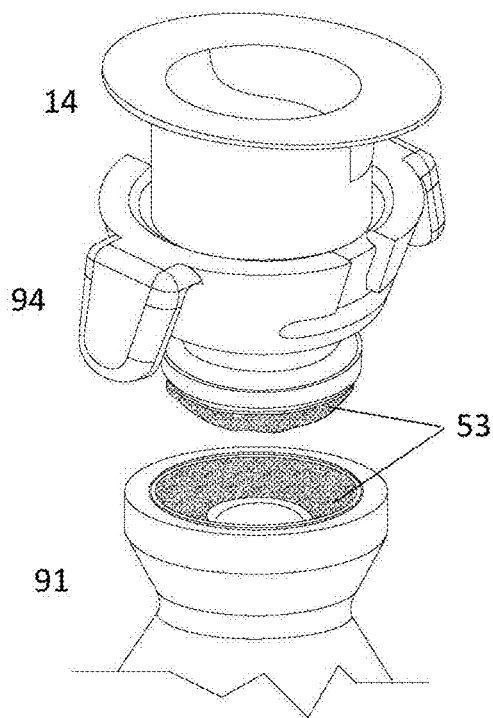
FIG. 17A illustrates a perspective view of a connector and socket having a hook and loop engagement according to one or more embodiments disclosed herein.
Figure 17B:
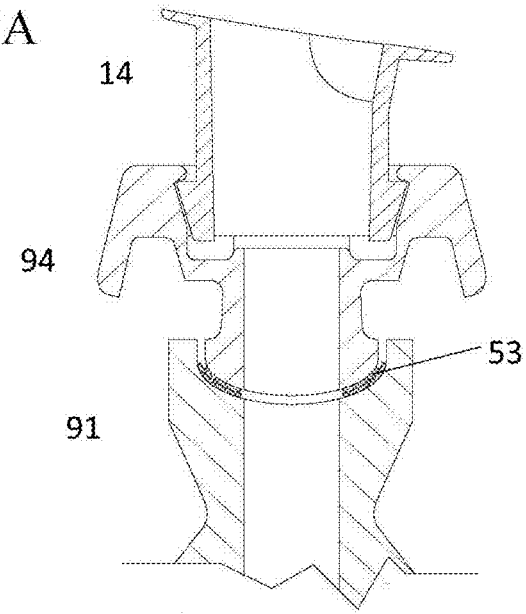
FIG. 17B illustrates a cross-sectional view of a connector and socket having a hook and loop engagement according to one or more embodiments disclosed herein.

Notably, the pincher 117 and handle portion 140 embodiments described herein with relation to the socket 94 and post 14 interaction could be applied to other components of the respiratory assembly 10 where selective engagement and/or coupling is desired. Other selective engagement and/or coupling mechanisms are also described herein and may be used with other components of the respiratory assembly 10 as well. Turning to FIGS. 16A-17B, the use of hook and loop fasteners for selectively coupling and decoupling components of the assembly 10 is depicted according to several embodiments of the invention; other embodiments coupling other components of the system 10 may be envisioned. For example, in FIGS. 16A and 16B, a connector 91 may include a hook fastener and a post 14 may include a loop fastener each shaped to nestingly engaged the other for selective coupling. In other embodiments, the connector body 92 may include the loop fastener and the post 14 may include a hook fastener. In FIGS. 17A and 17B, a socket 94 is coupled with the connector body 92 using hook and loop fasteners 53. The hook and loop fasteners 53 may also be used to couple the socket 94 with the post 14.

Figure 18:
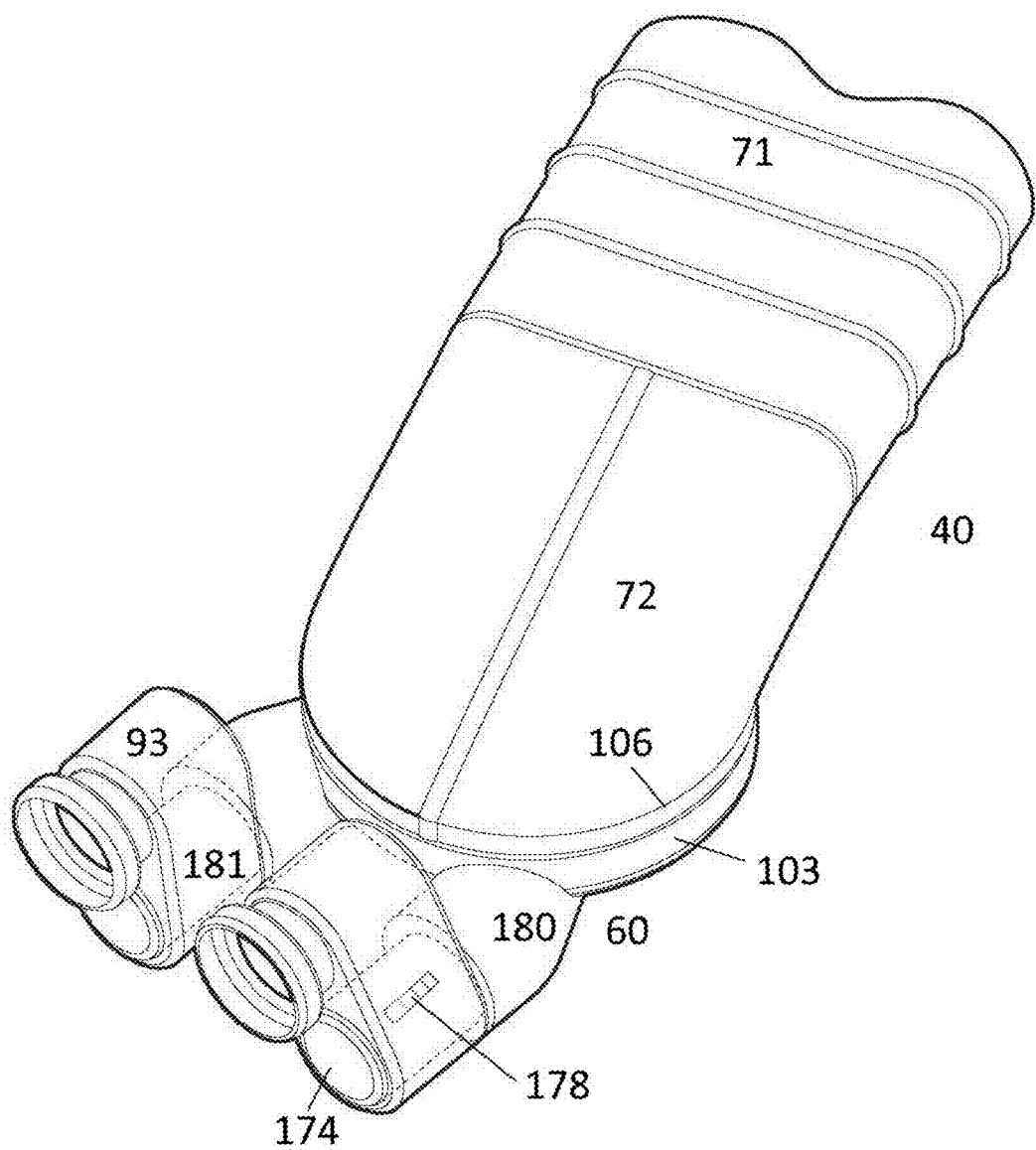
FIG. 18 illustrates a perspective view of a binocular-style respiratory assembly according to one or more embodiments disclosed herein.

In FIG. 18, a binocular-style assembly 10B is depicted. The hose 40 from the fluid source 41 may define a flexible portion 71 coupled to rigid portion 72. The rigid portion 72 may define a hose engagement 106 for engaging and/or rotatingly coupling with the splitter 60, a base 90 of the splitter 60, and/or a base tube engagement 103 of the splitter 60. The rotational coupling of the hose 40 and the splitter 60 with respect to each other permits customized positioning of the hose 40 when the assembly 10 and nasal assembly 12 are in use. The rotational coupling may include any of the connection embodiments described herein, including an embodiment where a mound of the base tube engagement 103 is nestingly engaged with a groove and/or lip of the hose engagement 106 for permitting the rigid portion 72 to be rotated about the splitter base 90 for desired positioning. A hermetic seal may be produced by the rotating coupling of the base tube engagement 103 and the hose engagement 106.

As with other embodiments of the splitter 60 described herein, the splitter 60 of FIG. 18 includes two connectors 91 extending from the splitter base 90. The connector body 92 of each connector 91 may define a first portion 180 extending from the splitter base 90 and a second portion 181 extending from the first portion 180. The second portion 181 may be configured for allowing the connector arm 93 to rotate about the second portion 181 for permitting customized positioning of the socket 94 with respect to the connector 91. A hermetic seal may be provided between the connector arm 93 and the connector body 92. Connector apertures 178 may be defined by the second portion 181 of the connector body 92 for permitting air flow between the second portion 181 and the connector arm 93. A connector end cap 174 may be defined by the second portion 181 for sealing a distal end of the second portion 181 and securing the connector arm 93 onto the second portion 181 to prevent sliding disengagement therefrom.

Each connector arm 93 may have less than forty-five degrees of rotation, less than ninety degrees of rotation, less than one-hundred and eighty degrees of rotation or a full three-hundred and sixty degrees of rotation with respect to the connector body 92. One or both of the connector arms 93 may be rotatable with respect to the connector body 92. By permitting the connector arm(s) 93 to rotate independently of each other and/or the connector body 92, the connector arm(s) 93 may be positioned to best fit the shape of a user's nose, whether the nose be wide or narrow, a single device may be used. A tension lock may be provided to lock the position of the connector arm(2) 93. In some embodiments, sufficient friction may permanently exist between the body 92 and arm 93 allowing the arm 93 to be rotated while maintaining its position when rotation is complete.

In some embodiments, the respiratory assembly 10, nasal assembly 12, mask assembly 20, and/or any components thereof may further include an oral device engagement for engaging an oral device engaged with the patient's mouth. For example, but not limited to, the patient may have a mouth guard, mandibular advancement splint or some other oral device that may be used in conjunction with the respiratory assembly 10, nasal assembly 12 and/or mask assembly 20. The oral device engagement may selectively engage the respiratory assembly 10, nasal assembly 12 and/or mask 10 to the oral device for stabilizing the position of the respiratory assembly 10, nasal assembly 12 and/or mask 10 with respect to the patient 1.

In one or more embodiments, the respiratory assembly 10, or any component thereof, may be provided as a short-term use product, such that the entire system is disposed of and replaced after a predetermined use period. For example, the respiratory assembly 10 may be configured for use as a three month use product, such that the patient receives a new respiratory assembly 10 every three months. In one embodiment, the post 14, cleat assembly 80 may be a disposable product. The patient may install a new adhesive pad 42 and sheet 30 after each use.

Figure 19A:
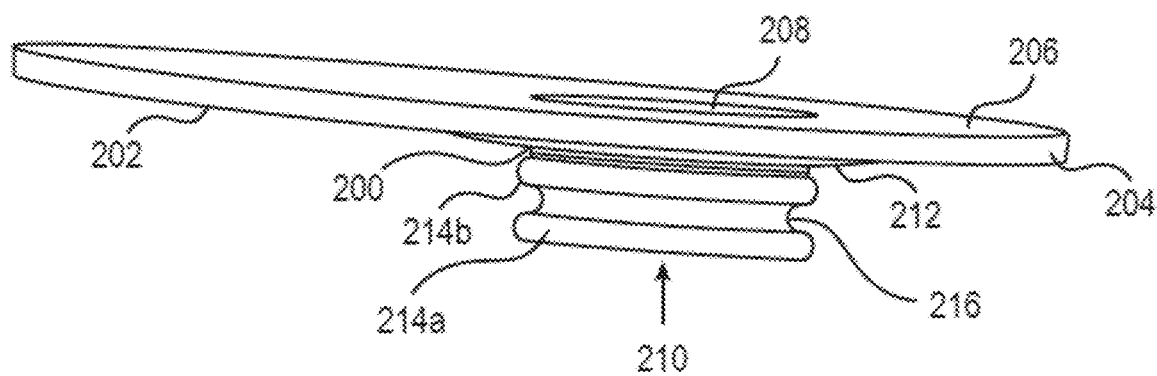
FIG. 19a illustrates an eyelet that can be used in accordance with some embodiments of the presently disclosed subject matter.

FIGS. 19a-19d illustrate an alternate embodiment of post 14. As shown in FIG. 19a, eyelet 200 is connected to non-contact face 202 of nasal strip 204 (e.g., the face not in contact with the user's skin). Contact face 206 interacts with and adheres to a nare of the user. Nasal strip 204 includes aperture 208, configured to align with the user's nasal passages. Aperture 208 provides a path for the flow of fluid from the disclosed respiratory assembly into the user's nasal passages without penetrating the nostril of the user.

Eyelet 200 can be constructed from any desired material. For example, in some embodiments, the eyelet can be constructed from a flexible material that easily bends and conforms to the shape of the user's nose. Suitable flexible materials can include (but are not limited to) rubber, foam, silicone, memory soft material, polymeric material, and combinations thereof.

Nasal strip 204 can include any medical grade tape or strip known or used in the art. For example, in some embodiments, the nasal strip can be a hydrocolloid tape, polyvinyl chloride foam tape, and/or polyolefin foam tape. The adhesive used on contact face 206 of strip 204 can include any known adhesive, such as (but not limited to) pressure-sensitive adhesives (such as acrylate adhesives), thermoplastic "hot melt" adhesives, elastomer-based adhesives, and acrylic adhesives, as would be known in the art.

Eyelet 200 can be connected to non-contact face 202 of nasal strip 204 using any known mechanism, such as the use of one or more adhesives, hook and loop closures (VELCRO®), cloth, ties, wraps, and the like. In some embodiments, the eyelet includes flange 212 that lies flat against the nasal strip non-contact face, providing a surface for the application of an adhesive. Eyelet 200 includes central opening 210 that extends longitudinally therethrough. The central opening is aligned with aperture 208 of the nasal strip to allow fluid flow from the respiratory assembly into the nasal passages of a user.

Eyelet 200 further includes proximal and distal radial projections 214a, 214b that extend about the circumference of the eyelet body and protrude outwards, thereby creating depression 216 therebetween. In some embodiments, projections 214a and 214b have a generally circular profile in cross-section, although other shapes can be included within the scope of the presently disclosed subject matter. Although two projections are shown in the Figures, the disclosed eyelet is not limited and can be configured with a single projection or with more than two projections.

Figure 19B:
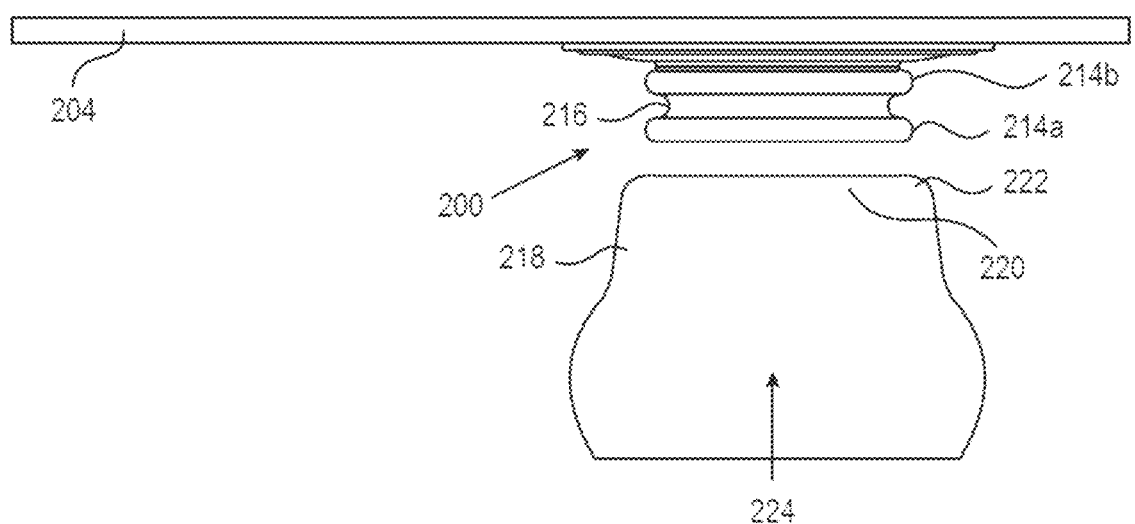
FIG. 19b illustrates an eyelet and a corresponding body in accordance with some embodiments of the presently disclosed subject matter.
Figure 19C:
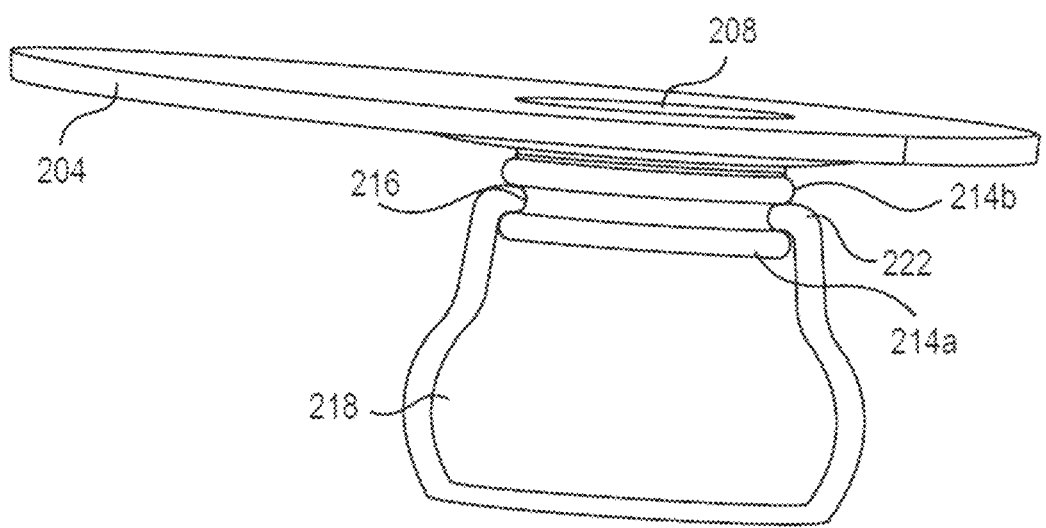
FIG. 19c illustrates a connected eyelet and body in accordance with some embodiments of the presently disclosed subject matter.

Projections 214a, 214b and depression 216 function to releasably retain a body by which fluids (e.g., gases) flow, as shown in FIG. 19b. Specifically, body 218 can be installed on the eyelet by pressing body opening 220 over proximal projection 214a. The body opening includes lip 222 with an inner diameter that is less than the diameter of the remainder of body internal recess 224. The internal diameter of opening 220 can be configured to approximate the outer diameter of eyelet depression 216. Thus, the internal diameter of opening 220 is necessarily smaller than the external diameter of projections 214. To attach the body to eyelet 200, lip 222 of the body is stretched over proximal projection 214a until the opening passes axially into depression 216. Body opening 220 then returns to its original, unstretched diameter, thereby retaining the body on the eyelet. Because the unstretched diameter of opening 220 is less than the external diameter of projections 214a, 214b, the body remains positioned between the projections, as shown in FIG. 19c.

When the user desires to remove the body from eyelet 200, he simply stretches opening 220 over proximal projection 214a. Nasal strip 204 and eyelet 200 can then be disposed of after use. In some embodiments, the eyelet and/or body 218 can be reused.

Figure 19D:
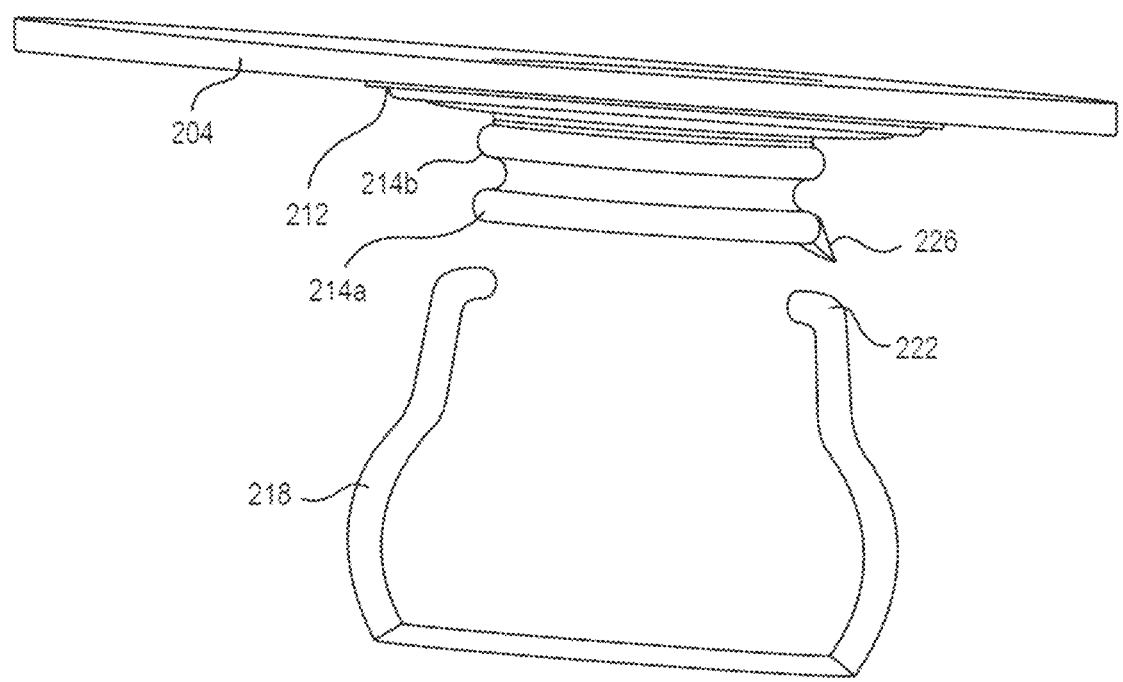
FIG. 19d illustrates one embodiment of an eyelet and a corresponding body in accordance with some embodiments of the presently disclosed subject matter.

In some embodiments, proximal projection 214a can comprises extension 226, as illustrated in FIG. 19d. The extension functions as a catch to allow for ease of use when connecting the body to the eyelet. Further, extension 226 increases the diameter of the proximal projection, thereby ensuring that the eyelet is retained on the body. Extension 226 can have any desired configuration, such as a barb and the like.

Figure 20A:
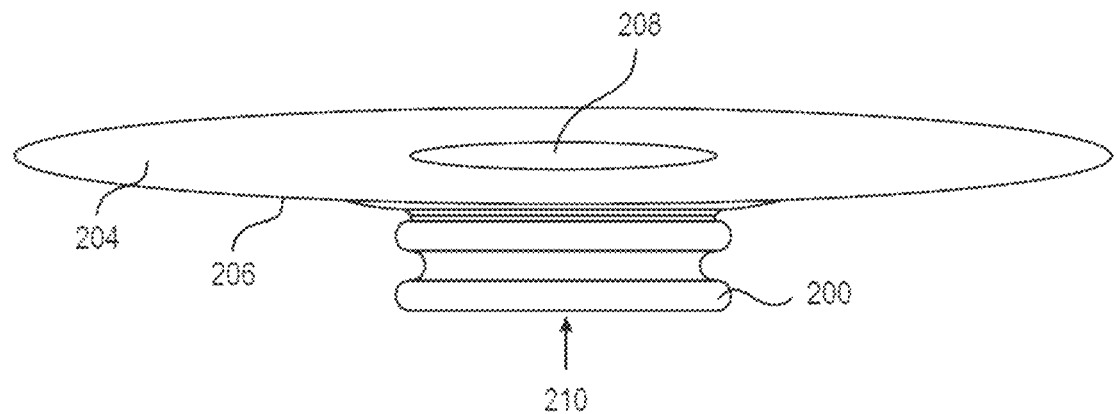
FIG. 20a is a perspective view of an eyelet in accordance with some embodiments of the presently disclosed subject matter.
Figure 20B:
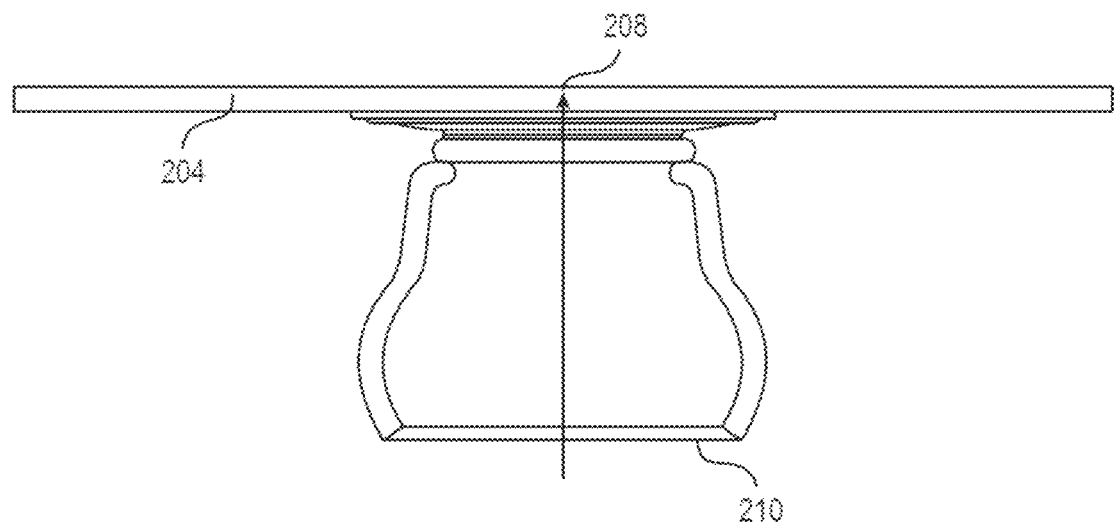

FIGS. 19a-19d illustrate one embodiment of eyelet 200 configured as a single unit used by one user nostril. However, the presently disclosed subject matter also includes embodiments wherein a single eyelet is shared by both nostrils, as shown in FIG. 20a. As illustrated, eyelet 200 can be connected to non-contact face 206 of nasal strip 204 (i.e., the face that does not contact the user's skin). The eyelet includes opening 210 that extends longitudinally therethough and aligns with apertures 208 of the nasal strip to allow fluid flow from the respiratory assembly into the nasal passages of the user. Aperture 208 can be sized and shaped to cover both nares of the user (e.g., both nostrils). Thus, fluid flows into eyelet central opening 210 where it is delivered to both user nostrils, as illustrated in FIG. 20b. The eyelet can therefore be configured as a "one size fits all" single unit eyelet or as a single larger port.

As described above, the body is used to flow fluids (e.g., gases) through the eyelet and into the user's nostrils. Body 218 attaches around or to the eyelet to provide a path for fluid flow. As shown in FIGS. 19b and 19c, the body can be configured to connect to a single eyelet. However, the body can be configured in a dual embodiment with a connector that engages into a single or double port socket. The port socket can therefore be one single unit that accommodates both user nostrils through a single body that connects to a single eyelet or both eyelets. Alternatively, the port socket can be configured with two units joined by a connector, wherein each unit accommodates a single user nostril through a body that connects to a single eyelet. The connections can be accomplished through any known mechanism, such as (but not limited to) the use of adhesive tape, hook and loop closures (VELCRO®), cloth, ties, wraps, and the like.

Eyelet 200 and/or port tip 218 can be constructed from any desired material. For example, in some embodiments, the eyelet and/or port tip can comprise an elastomeric material that is extensible or elongates in at least one direction upon the application of a biasing force and returns to its original dimensions once the force is removed. Any suitable elastomeric material can be used, including (but not limited to) natural rubber, synthetic rubber, polyurethane, acrylic, vinyl, nitrile rubber, butadiene rubber, styrene-butadiene rubber, acetate, and the like.

While the embodiments have been described in connection with the preferred embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims.

The invention claimed is:
1. A respiratory assembly comprising:
 at least one connector, wherein a base is in fluid communication with a hose or fluid source for allowing gaseous flowthrough between the at least one connector, the base, and the hose or fluid source;
 a pair of sockets separable from the at least one connector, wherein the sockets are selectively engaged with the at least one connector, wherein each socket is independently movable relative to the other socket, wherein each socket defines:
a collar comprising a socket tip for receiving a respective eyelet that is configured to connect to a user's nare such that the eyelet does not extend into a respective nostril when the eyelet is connected to a user's nare;
a cavity extending through the collar;
wherein the collar has a first mode of operation in which the socket tip is engaged with an eyelet and a second mode of operation in which the socket tip is not engaged with the eyelet through retraction of the socket tip in response to manipulation by a user,
wherein the respiratory assembly is maskless such that fluid from the hose or fluid source flows through the connector into the user's nares but not into the user's mouth when the respiratory assembly is worn by the user.

2. The respiratory assembly of claim 1, wherein the socket tip includes a lip configured to releasably engage with a proximal projection positioned at a proximal end of the eyelet that faces the at least one connector, wherein the eyelet includes a distal projection positioned at a distal end of the eyelet that faces a user's nare, and a depression that extends about a circumference of the eyelet.

3. The respiratory assembly of claim 2, wherein the lip has an inner diameter that is less than the outer diameter of the distal and proximal projections.

4. The respiratory assembly of claim 2, wherein the proximal projection comprises a barb.

5. The respiratory assembly of claim 1, wherein the socket is constructed from an elastomeric material.

6. The respiratory assembly of claim 5, wherein the elastomeric material is selected from natural rubber, synthetic rubber, polyurethane, acrylic, vinyl, nitrile rubber, butadiene rubber, styrene-butadiene rubber, acetate, and combinations thereof.

7. The respiratory assembly of claim 1, wherein the eyelet comprises a flange that is connected to a nasal strip configured to releasably attach to a user's nare.

8. The respiratory assembly of claim 1, wherein the eyelet comprises a body defined by a proximal projection and a distal projection that extend about a circumference of the body, and a depression positioned between the proximal and distal projections, wherein the proximal projection is positioned at a proximal end of the eyelet that faces the at least one connector, wherein the distal projection is positioned at a distal end of the eyelet that faces a user's nare.

9. The respiratory assembly of claim 1, wherein the base defines four openings for engaging two connectors and two caps.

10. The respiratory assembly of claim 1, further comprising vents for titrating fluids.

11. A method of providing fluid to a patient's nasal passages, the method comprising:
releasably attaching a socket tip of a respiratory assembly to an eyelet that is configured to connect to a patient's nare; wherein the respiratory assembly comprises:
at least one connector, wherein a base is in fluid communication with a hose or fluid source for allowing gaseous flowthrough between the at least one connector, the base, and the hose or fluid source;
a pair of sockets separable from the at least one connector, wherein the sockets are selectively engaged with the at least one connector, wherein each socket is independently movable relative to the other socket, wherein each socket defines:
a collar comprising a socket tip for receiving a respective eyelet that is configured to connect to the patient's nare such that the eyelet does not extend into a respective nostril when the eyelet is connected to a user's nare;
a cavity extending through the collar;
wherein the collar has a first mode of operation in which the socket tip is engaged with an eyelet and a second mode of operation in which the socket tip is not engaged with the eyelet through retraction of the socket tip in response to manipulation by a user;
wherein the respiratory assembly is maskless such that fluid from the hose or fluid source flows through the connector into the patient's nares but not into the patient's mouth when the respiratory assembly is worn by the patient;
releasably attaching the eyelet to the patient's nare;
initiating flow of fluid from the fluid source, whereby fluid is provided to the patient's nasal passages.

12. The method of claim 11, wherein the fluid is ambient air or oxygen enriched air.

13. The method of claim 11, wherein the socket tip includes a lip configured to releasably engage with a proximal projection positioned at a proximal end of the eyelet that faces the at least one connector, wherein the eyelet includes a distal projection positioned at a distal end of the eyelet that faces a user's nare, and a depression that extends about a circumference of the eyelet.

14. The method of claim 13, wherein the proximal projection comprises a barb.

15. The method of claim 13, wherein the lip has an inner diameter that is less than the outer diameter of the distal and proximal projections.

16. The method of claim 11, wherein the socket is constructed from an elastomeric material.

17. The method of claim 16, wherein the elastomeric material is selected from natural rubber, synthetic rubber, polyurethane, acrylic, vinyl, nitrile rubber, butadiene rubber, styrene-butadiene rubber, acetate, and combinations thereof.

18. The method of claim 11, wherein the eyelet comprises a flange that is connected to a nasal strip configured to releasably attach to a user's nare.

19. The method of claim 11, wherein the eyelet comprises a body defined by a proximal projection and a distal projection that extend about a circumference of the body, and a depression positioned between the proximal and distal projections, wherein the proximal projection is positioned at a proximal end of the eyelet that faces the at least one connector, wherein the distal projection is positioned at a distal end of the eyelet that faces a user's nare.

20. The method of claim 11, wherein the respiratory assembly further comprising vents for titrating fluids.

* * * * *